(12) United States Patent
Maltsev et al.

(10) Patent No.: US 9,506,032 B2
(45) Date of Patent: Nov. 29, 2016

(54) ENGINEERED BIOLOGICAL PACEMAKERS

(75) Inventors: Victor Maltsev, Parkville, MD (US); Edward G. Lakatta, Bel Air, MD (US); Ihor Zahanich, Towson, MD (US); Syevda Sirenko, Dortmund (DE); Maxim Mikheev, Pittsburgh, PA (US); Yoram Vodovotz, Sewickley, PA (US)

(73) Assignees: The United States of America, as represented by the Secretary, Department of Health and Human Services, Washington, DC (US); University of Pittsburgh—of The Commonwealth System of Higher Education, Pittsburgh, PA (US)

( * ) Notice: Subject to any disclaimer, the term of this patent is extended or adjusted under 35 U.S.C. 154(b) by 661 days.

(21) Appl. No.: 13/322,066

(22) PCT Filed: May 21, 2010

(86) PCT No.: PCT/US2010/035823
§ 371 (c)(1),
(2), (4) Date: Feb. 6, 2012

(87) PCT Pub. No.: WO2010/135676
PCT Pub. Date: Nov. 25, 2010

(65) Prior Publication Data
US 2012/0134971 A1 May 31, 2012

Related U.S. Application Data

(60) Provisional application No. 61/180,491, filed on May 22, 2009.

(51) Int. Cl.
C12N 5/077 (2010.01)
A61K 48/00 (2006.01)
C12N 15/86 (2006.01)

(52) U.S. Cl.
CPC ........... *C12N 5/0657* (2013.01); *A61K 48/005* (2013.01); *C12N 15/86* (2013.01); *C12N 2500/14* (2013.01); *C12N 2501/01* (2013.01); *C12N 2506/02* (2013.01); *C12N 2510/00* (2013.01); *C12N 2740/15043* (2013.01); *C12N 2830/002* (2013.01)

(58) Field of Classification Search
None
See application file for complete search history.

(56) References Cited

U.S. PATENT DOCUMENTS

| | | | |
|---|---|---|---|
| 6,214,620 B1 | 4/2001 | Johns et al. | |
| 6,376,471 B1 | 4/2002 | Lawrence, III et al. | |
| 7,103,418 B2 | 9/2006 | Laske et al. | |
| 2002/0022259 A1 | 2/2002 | Lee et al. | |
| 2004/0266675 A1* | 12/2004 | Anderson | 514/12 |

FOREIGN PATENT DOCUMENTS

| | | |
|---|---|---|
| EP | 2 105 142 A1 | 9/2009 |
| WO | WO 98/02150 A1 | 1/1998 |
| WO | WO 02/087419 A2 | 11/2002 |
| WO | WO 02/098286 A2 | 12/2002 |
| WO | WO 2005/062890 A2 | 7/2005 |
| WO | WO 2005/062958 A2 | 7/2005 |
| WO | WO 2007/014134 A2 | 2/2007 |

OTHER PUBLICATIONS

Martin et al., Sudden Cardiac Death and Inherited Channelopathy: the Basic Electrophysiology of the Myocyte and Myocardium in Ion Channels, Heart, 2012. 98:536-543.*
Ciaccio et al. Detection of the Diastolic Pathway, Circuit Morphology and Inducibility of HUman Post-Infarction Ventricular Tachycardia from Mapping in Sinus Rhythm. Heart Rhythm, 2008. 5(7): 981-991).*
Kurokawa, Compartmentalization of Ion channels in the Heart. Biological Pharm. Bull.,2007. 30(12):2231-2237.*
Kuznetsova, Regulatory Properties of Adenyly Cyclase Isoforms. Journal of Evolutionary Biochemistry and Physiology, 2002. 38(4):289-304, at least pp. 379-383.*
Xiao. Cell and Gene Therapy for Arrhythmas: Repair of Cardiac Conduction Damage. Journal of Geriatric Cardiology, 2011. 8:147-158.*
Bestor. Gene Silencing as a Threat to the Success of Gene Therapy. Journal of Clinical Investigation, 2000. 105:409-411.*
Rosen et al, Biological Pacemakers based on If. Med. Bio. Compt., 2007. 45:157-166.*
Gao et al. Adenylcyclase Increases Responsiveness to Catecholamine Stimulation in Transgenic Mice. Circulation, 1999. 99:1618-1622.*
Bers, Donald M. Calcium and Cardiac Rhythms, Circulation research, 2002. 90:14-17.*
Grueter, CaMKII, An Emerging Molecular Driver for Calcium Homeostasis, Arrhythmias, and Cardiac Function. Journal of Molecular Medicine, 2007. 85:5-14.*
Rigg, et al. Modulation of the Hyperpolarization-Activated Current (If) by Calcium and Calmodulin in the Guinea-Pig Sino-Atrial Node. Cardiovascular Research, 2003. 57:497-504.*
Mattick et al. Ca2+-stimulated adenylyl cyclase isoform AC1 is preferentially expressed in guinea-pig sino-atrial node cells and modulates the If pacemaker current. Journal of Physiology, 2007. 582(3):1195-1203.*
Tang et al, Adenylyl cyclase type VI corrects cardiac sarcoplasmic reticulum calcium uptake defects in cardiomyopathy. American Journal of Physiology Heart Circulation Physiology, 2004. 287:H1906-H1912.*
Vinogradova et al, Constitutive Phosphodiesterase Activity Restricts Spontaneous Beating Rate of Cardiac Pacemaker Cells by Suppressing Local Ca2+ Releases, Circulation Research, 2008. 102:761-769.*

(Continued)

*Primary Examiner* — Maria Leavitt
*Assistant Examiner* — Kimberly A Aron
(74) *Attorney, Agent, or Firm* — Swanson & Bratschun, L.L.C.

(57) ABSTRACT

Biological pacemakers engineered to intrinsically generate rhythmic excitations are disclosed. In addition, methods of producing the biological pacemakers are disclosed. Methods of treating or preventing arrhythmia and heart disease associated with a defective pacemakers are also disclosed.

9 Claims, 11 Drawing Sheets

(56) References Cited

OTHER PUBLICATIONS

Maltsev and Lakatta, Dynamic Interactions of an intracellular Cs2+ clock and membrane ion channel clock underlie robus initiation and regulation of cardiac pacemaker function. Cardiovacular Research, 2008. 77:274-284. available online Nov. 2007.*
Younes et al. Ca2+-Stimulated Basal Adenylyl Cyclase Activity Localization in Membrane Lipid Microdomains of Cardiac Sinoatrial Nodal Pacemaker Cells. JBC, 2008. 283(21):14461-14468.*
Vinogradova et al. Rhythmic Ca2+ Oscillations Drive Sinoatrial Nodal Cell Pacemaker Function to Make the Heart Tick. Annals of NY Academy of Sciences, 2005. 1047:138-156.*
Zhang et al. Stem Cell-Derived Cardiomyocytes Demonstrate Arrhythmic Potential. Circulation, 2002. 106:1294-1299.*
Matkar et al, Cardiac Gene Therapy: are we there yet? Gene Therapy, 2016, pp. 1-14.*
Georget et al. Augmentation of cardiac contractility with No Change in L-type Ca2+ Current in transgenic Mice with a Cardiac-Directed Expression of the Human Adenylyl Cyclase type 8 (AC8). FASEB Journal, 2002. 21 pages.*
Zahanich I, et al., "Rhythmic beating of stem cell-derived cardiac cells requires dynamic coupling of electrophysiology and Ca cycling", J Mol Cell Cardiol, Jan. 2011, 50(1), 66-76 [Epub Oct. 15, 2010].
Bround MJ, et al., "Cardiac ryanodine receptors control heart rate and rhythmicity in adult mice", Cardiovasc Res. Sep. 14, 2012. [Epub ahead of print].
Yaniv Y, et al., "Beat-to-beat Ca(2+)-dependent regulation of sinoatrial nodal pacemaker cell rate and rhythm", J Mol Cell Cardiol, Dec. 2011, 51(6):902-5 [Epub Sep. 14, 2011].
Liu J, et al., "A full range of mouse sinoatrial node AP firing rates requires protein kinase A-dependent calcium signaling", J Mol Cell Cardiol, Nov. 2011, 51(5):730-9 [Epub Aug. 4, 2011].
Yaniv Y, et al., "Crosstalk between mitochondrial and sarcoplasmic reticulum Ca2+ cycling modulates cardiac pacemaker cell automaticity", PLoS One. 2012, 7(5):e37582 [Epub May 29, 2012] doi:10.1371/journal.pone.0037582.
Maltsev VA, Lakatta EG, "The funny current in the context of the coupled-clock pacemaker cell system", Heart Rhythm, Feb. 2012, 9(2):302-7 [Epub Sep. 16, 2011].
Maltsev AV, et al., "Synchronization of stochastic $Ca^2(+)$ release units creates a rhythmic $Ca^2(+)$ clock in cardiac pacemaker cells", Biophys J., Jan. 19, 2011,100(2):271-83.
Lakatta EG, et al., "A coupled System of intracellular Ca2+ clocks and surface membrane voltage clocks controls the timekeeping mechanism of the heart's pacemaker", Circ Res. Mar. 2010,106(4):659-73.
Vinogradova TM, et al., "Sarcoplasmic reticulum Ca2+ pumping kinetics regulates timing of local Ca2+ releases and spontaneous beating rate of rabbit sinoatrial node pacemaker cells", Circ Res., Sep. 17, 2010, 107(6):767-75. [Epub Jul. 22, 2010].
Maltsev VA, Lakatta EG., "Yin and yang of the cardiac pacemaker clock system in health and disease", Heart Rhythm, Jan. 2010, 7(1):96-8. [Epub Nov. 10, 2009].
Maltsev VA, Lakatta EG. "Funny current provides a relatively modest contribution to spontaneous beating rate regulation of human and rabbit sinoatrial node cells", J Mol Cell Cardiol. Apr. 2010, 48(4):804-6. [Epub Dec. 28, 2009].
Maltsev VA, Lakatta EG. "A novel quantitative explanation for the autonomic modulation of cardiac pacemaker cell automaticity via a dynamic system of sarcolemmal and intracellular proteins," Am J Physiol Heart Circ Physiol, Jun. 2010, 298(6):H2010-23 [Epub Mar. 12, 2010].
Boink, G.J. et al., "Ca(2+)-stimulated adenylyl cyclase AC1 generates efficient biological pacing as single gene therapy and in combination with HCN2", Circulation, Jul. 31, 2012, 126(5): 528-536. [Epub Jun. 29, 2012].

Abi-Gerges et al., "Functional expression and regulation of the hyperpolarization activated non-selective cation current in embryonic stem cell-derived cardiomyocytes", J. Physiol. Mar. 1, 2000, 523(Pt 2), 377-389.
Anghel et al., "Creating a cardiac pacemaker by gene therapy", Medical & Biological Engineering & Computing, (no month) 2007, 45(2), 145-155, XP002606225.
Benson et al., "GenBank", Nucleic Acids Res., Jan. 1, 1997, 25(1), 1-6.
Bogdanov et al., "Sinoatrial nodal cell ryanodine receptor and Na+-Ca2+ exchanger: molecular partners in pacemaker regulation", Circ Res., Jun. 22, 2001, 88(12), 1254-1258.
Dolnikov et al., "Functional properties of human embryonic stem cell-derived cardiomyocytes: intracellular Ca2+ handling and the role of sarcoplasmic reticulum in the contraction", Stem Cells, Feb. 2006, 24(2), 236-245.
Fan et al., "Perforated patch recording with beta-escin", Pflugers Arch., Nov. 1998, 436(6), 1021-1023.
Fu et al., "Crucial role of the sarcoplasmic reticulum in the developmental regulation of Ca2+ transients and contraction in cardiomyocytes derived from embryonic stem cells", Faseb J., Jan. 2006, 20(1), 181-183.
Gene Targeting Protocols, Kmeic 2ed. pp. 1-35 (2000).
Gene Transfer and Expression Protocols, Murray ed., pp. 109-206 (1991).
Gene Transfer and Expression Protocols, vol. 7, Murray ed. pp. 81-89 (1991).
Goldspiel et al., "Human gene therapy", Clin Pharm., Jul. 1993, 12(7), 488-505.
Guzman, "Efficient gene transfer into myocardium by direct injection of adenovirus vectors", Circ Res., Dec. 1993, 73(6), 1202-1207.
Gyorke et al., "Regulation of sarcoplasmic reticulum calcium release by luminal calcium in cardiac muscle", Front Biosci., Jun. 1, 2002, 7, 1454-1463.
He et al., "Human embryonic stem cells develop into multiple types of cardiac myocytes: action potential characterization", Circ Res., Jul. 11, 2003, 93(1), 32-39.
Ji et al., "Regulation of the L-type Ca2+ channel during cardiomyogenesis: switch from NO to adenylyl cyclase-mediated inhibition", Faseb J., Feb. 1999, 13(2), 313-324.
Kapur et al., "Inositol-1,4,5-trisphosphate-mediated spontaneous activity in mouse embryonic stem cell-derived cardiomyocytes", J. Physiol., Jun. 15, 2007, 581(Pt 3),1113-1127.
Kehat et al., "Electromechanical integration of cardiomyocytes derived from human embryonic stem cells", Nat Biotechnol. , Oct. 2004, 22(10), 1282-1289.
Klug et al., "Genetically selected cardiomyocytes from differentiating embryonic stem cells form stable intracardiac grafts", J. Clin Invest., Jul. 1, 1996, 98(1), 216-224.
Kolossov et al., "Identification and characterization of embryonic stem cell-derived pacemaker and atrial cardiomyocytes", Faseb J., Apr. 2005, 19(6), 577-579.
Koushik et al., "Targeted inactivation of the sodium-calcium exchanger (Ncx1) results in the lack of a heartbeat and abnormal myofibrillar organization", Faseb J., May 2001, 15(7), 1209-1211.
Lakatta et al., "A coupled System of intracellular Ca2+ clocks and surface membrane voltage clocks controls the timekeeping mechanism of the heart's pacemaker", Circ Res., Mar. 5, 2010, 106(4), 659-673.
Lakatta et al., "The Integration of Spontaneous Intracellular Ca2+ Cycling and Surface Membrane Ion Channel Activation Entrains Normal Automaticity in Cells of the Heart's Pacemaker", Ann NY Acad Sci., Oct. 2006, 1080, 178-206.
Lakatta et al., "The missing link in the mystery of normal automaticity of cardiac pacemaker cells", Ann NY Acad Sci., Mar. 2008, 1123, 41-57.
LaPointe et al., "Left ventricular targeting of reporter gene expression in vivo by human BNP promoter in an adenoviral vector", Am J. Physiol Heart Circ Physiol., Oct. 2002, 283(4), H1439-H1445.
Lyashkov et al., "Calcium cycling protein density and functional importance to automaticity of isolated sinoatrial nodal cells are independent of cell size", Circ Res., Jun. 2007, 100, 1723-1731.

(56) References Cited

OTHER PUBLICATIONS

Lyashkov et al., "Role of acetylcholine-activated potassium current (IKAch), hyperpolarization-activated current (If), Protein Kinase A (PKA)-dependent phosphorylation and Ca2+cycling in muscarinic receptor (M2R) regulation of spontaneous Action Potential Rate (APR) in isolated rabbit Sinoatrial Node Cells (SANC)", Biophys J., 2008, Supplement 251 (Abstract).

Maltsev et al., "Cardiomyocytes differentiated in vitro from embryonic stem cells developmentally express cardiac-specific genes and ionic currents", Circ Res., Aug. 1994, 75(2), 233-244.

Maltsev et al., "Dynamic interactions of an intracellular Ca2+ clock and membrane ion channel clock underlie robust initiation and regulation of cardiac pacemaker function", Cardiovasc Res., Nov. 5, 2008, 77(2), 274-284.

Maltsev et al., "Embryonic stem cells differentiate in vitro into cardiomyocytes representing sinusnodal, atrial and ventricular cell types", Mech Dev., Nov. 1993, 44(I), 41-50.

Maltsev et al., "Establishment of beta-adrenergic modulation of L-type Ca2+ current in the early stages of cardiomyocyte development", Circ Res., Feb. 5, 1999, 84(2), 136-145.

Maltsev et al., "Synergism of coupled subsarcolemmal Ca2+ clocks and sarcolemmal voltage clocks confers robust and flexible pacemaker function in a novel pacemaker cell model", Am J. Physiol Heart Circ Physiol., Jan. 2009, 296:H594-H615.

Maltsev et al., "The emergence of a general theory of the initiation and strength of the heartbeat", J. Pharmacol Sci., 2006,100(5), 338-369.

Marban et al., "Creation of a biological pacemaker by gene- or cell-based approaches", Medical & Biological Engineering & Computing, Feb. 2007, 45(2), 133-144, XP002606211.

Mery et al., "Initiation of embryonic cardiac pacemaker activity by inositol 1,4,5-trisphosphate-dependent calcium signaling", Mol Biol Cell, May 2005, 16(5), 2414-2423.

Miake et al., "Biological pacemaker created by gene transfer", Nature, Sep. 12, 2002, 419(6903), 132-133.

Morgan et al., "Human gene therapy", Annu Rev Biochem., 1993, 62, 191-217.

Mulligan, "The basic science of gene therapy", Science, May 14, 1993, 260(5110), 926-932.

Otsu et al., "Na+/K+ ATPase and its: functional coupling with Na+/Ca2+ exchanger in mouse embryonic stem cells during differentiation into cardiomyocytes", Cell Calcium., Feb. 2005, 37(2), 137-151.

Rapila et al., "Excitation-contraction coupling of the mouse embryonic cardiomyocyte", J. Gen Physiol., Oct. 2008, 132(4), 397-405.

Reppel et al., "Functional expression of the Na+/Ca2+ exchanger in the embryonic mouse heart", J. Mol Cell Cardiol., Jan. 2007, 42(1), 121-132.

Robinson et al., "Gene Therapy—Proceeding From Laboratory to Clinic", TIBTECH, May 1993, 11(5), 155-215.

Rosen et al., "Conference report: building a biologic pacemaker", J Electrocardiol., Nov.-Dec. 2007, 40(6 Suppl), S197-S198.

Rosen et al., "Genes, stem cells and biological pacemakers", Cardiovasc Res., Oct. 1, 2004, 64(1), 12-23.

Ruhparwar et al., "Adenylate-cyclase VI transforms ventricular cardiomyocytes into biological pacemaker cells", Circulation, Oct. 2007, 116(16 Suppl. S), 368, 80th Annual Scientific Session of the American-Heart-Association, Orlando, FL, USA, Nov. 4-7, 2007, XP009140319.

Ruhparwar et al., "Enrichment of cardiac pacemaker-like cells: neuregulin-1 and cyclic AMP increase I(f)-current density and connexin 40 mRNA levels in fetal cardiomyocytes", Med Biol Eng Comput., Feb. 2007, 45(2), 221-227.

Sartiani et al., "Developmental changes in cardiomyocytes differentiated from human embryonic stem cells: a molecular and electrophysiological approach", Stem Cells, May 2007, 25(5), 1136-1144.

Sasse et al., "Intracellular Ca2+ oscillations, a potential pacemaking mechanism in early embryonic heart cells", J. Gen Physiol., Aug. 2007, 130(2), 133-144.

Satin et al., "Calcium Handling in Human Embryonic Stem Cell Derived Cardiomyocytes", Stem Cells, Aug. 2008, 26(8), 1961-1972.

Satin et al., "Mechanism of spontaneous excitability in human embryonic stem cell derived cardiomyocytes", J. Physiol., Sep. 1, 2004, 559(Pt 2), 479-496.

Sauer et al, "Characteristics of calcium sparks in cardiomyocytes derived from embryonic stem cells", Am J. Physiol. Heart Circ. Physiol., Jul. 2001, 281(1), H411-H421.

Schuldt et al., "Repairing damaged myocardium: evaluating cells used for cardiac regeneration", Curr Treat Options Cardiovasc Med., Feb. 2008, 10(1), 59-72.

Song et al., "Ca2+ signaling in cardiac myocytes overexpressing the alpha-1 subunit of L-type Ca?+ channel", Circ Res., Feb. 8, 2002, 90(2),174-181.

Tolstoshev , "Gene therapy, concepts, current trials and future directions", Annu Rev Pharmacol Toxicol., 1993, 33,573-596.

Tsien et al., "Cellular and subcellular mechanisms of cardiac pacemaker oscillations", J. Exp Biol., Aug. 1979, 81, 205-215.

Viatchenko-Karpinski et al., "Intracellular Ca2+ oscillations drive spontaneous contractions in cardiomyocytes during early development", Proc Natl Acad Sci USA, Jul. 6, 1999, 96(14), 8259-8264.

Vinogradova et al., "Constitutive phosphodiesterase activity restricts spontaneous beating rate of cardiac pacemaker cells by suppressing local Ca2+ releases", Circ Res., Apr. 2008, 102, 761-769.

Vinogradova et al., "High basal protein kinase A-dependent phosphorylation drives rhythmic internal Ca2+ store oscillations and spontaneous beating of cardiac pacemaker cells", Circ Res., Mar. 3, 2006, 98(4), 505-514.

Vinogradova et al., "Rhythmic ryanodine receptor Ca2+ releases during diastolic depolarization of sinoatrial pacemaker cells do not require membrane depolarization", Circ Res., Apr. 2, 2004, 94(6), 802-809.

Vinogradova et al., "Sinoatrial node pacemaker activity requires Ca(2+)/calmodulin-dependent protein kinase II activation", Circ Res., Oct. 27, 2000, 87(9), 760-767.

Wu et al., "Calmodulin kinase II is required for fight or flight sinoatrial node physiology", Proc Natl Acad Sci USA, Apr. 7, 2009, 106(14), 5972-5977, Epub. Mar. 10, 2009.

Xue et al., "Functional integration of electrically active cardiac derivatives from genetically engineered human embryonic stem cells with quiescent recipient ventricular cardiomyocytes: insights into the development of cell-based pacemakers", Circulation, Jan. 4, 2005, 111(1), 11-20.

Yanagi et al., "Hyperpolarization-activated cyclic nucleotide-gated channels and T-type calcium channels confer automaticity of embryonic stem cell-derived cardiomyocytes", Stem Cells, Nov. 2007, 25(11), 2712-2719.

Yang et al., "Reduced sinoatrial cAMP content plays a role in postnatal heart rate slowing in the rabbit", Clin Exp Pharmacol Physiol., Aug. 2006, 33(8),757-762.

Yang et al., "The ryanodine receptor modulates the spontaneous beating rate of cardiomyocytes during development", Proc Natl Acad Sci USA, Jul. 9, 2002, 99(14), 9225-9230.

Zhang et al., "Stem cell-derived cardiomyocytes demonstrate arrhythmic potential", Circulation, Sep. 3, 2002, 106(10),1294-1299.

\* cited by examiner

A "Rhythmically" beating cell

B "Dysrhythmic" cell

C

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctaccgggta ggggaggcgc                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcgaaaggc ccggagatga                                              20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctgtgcccc agtttgctag                                              20

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcatctccgg gcctttcgac accggtcgcc accatgg                           37

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tacttagtta cccgggggagc                                             20

<210> SEQ ID NO 6
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctagcaaact ggggcacagc gagggcagag gaagtcttct aacatgcggt gacgtggagg  60

```
agaatcccgg ccctatgtct agactggaca agag                                      94

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggggacaagt ttgtacaaaa aagcaggctt aatttttttc actgcctcg                      49

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggggacaact tttgtataca aagttgtagg ctggatcggt cccgg                          45

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggggacaact tgtatacaa aagttgtgcg ccaccatgag cggggg                          46

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggggacaact tgtatagaa aagttgggtg ccctgtaca gctcgtccat                       50

<210> SEQ ID NO 11
<211> LENGTH: 102
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggggacaact tttctataca aagttgcttg agggcagagg aagtcttcta acatgcggtg          60
acgtggagga gaatcccggc cccgccacca tggagctctc cg                            102

<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 12
ggggacaact ttattataca aagttgtccc tatggcaaat cagatttgtc                    50

<210> SEQ ID NO 13
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggggacaact ttgtataata aagttgctgc tagcgctacc ggactc                        46

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggggaccact ttgtacaaga aagctgggta accggtggat cccgggc                       47
```

ENGINEERED BIOLOGICAL PACEMAKERS

CROSS-REFERENCE TO RELATED APPLICATIONS

This application is the National Stage of International Patent Application No. PCT/US2010/035823 filed May 21, 2010, which claims the benefit of U.S. Provisional Patent Application No. 61/180,491, filed May 22, 2009, the disclosures of which are incorporated herein by reference in their entireties.

STATEMENT OF FEDERALLY SPONSORED RESEARCH

The U.S. Government may have certain rights in the invention described herein, which was made in part with funds from NIH Contract No. HHSN263200700019I.

SEQUENCE LISTING

The instant application contains a Sequence Listing which has been submitted in ASCII format via EFS-Web and is hereby incorporated by reference in its entirety. Said ASCII copy, created on Feb. 1, 2012, is named NIHA0462.txt and is 3,728 bytes in size.

FIELD OF THE INVENTION

The present invention relates to biological pacemakers. More specifically, the invention relates to biological pacemakers engineered to intrinsically generate rhythmic electric excitations, methods of producing the biological pacemakers, and methods of treating or preventing arrhythmia and heart disease associated with a defective pacemaker.

BACKGROUND OF THE INVENTION

Cardiac contraction in a healthy human heart is initiated by spontaneous excitation of the sinoatrial ("SA") node located in the right atrium. The electric impulse generated by the SA node travels to the atrioventricular ("AV") node where it is transmitted to the bundle of His and to the Purkinje network. The fibers in the Purkinje network branch out in many directions to facilitate coordinated contraction of the left and right ventricles. In some disease states, the heart loses some of its natural capacity to pace properly. Such dysfunction is commonly treated by implanting an electronic pacemaker.

While effectively improving the lives of many patients, implantable pacemakers have certain limitations. For example, implantable pacemakers rely on a self-contained power source such as a battery and consequently have a limited lifetime before the power source is in need of replacement. Hence, an otherwise healthy patient may require multiple surgeries to replace the power source or the entire implantable pacemaker. Also, implantable pacemakers may not directly respond to physiological signals similar to the way the SA node responds to such signals. Furthermore, there is the risk of infections associated with implantable pacemakers, which, while infrequent, can be catastrophic. Also, there is the potential for interference from other devices.

These problems could be solved with the creation of biological (i.e., cell-based) cardiac pacemakers that would be naturally integrated into or created within the heart with deficient pacemaker function. While many cell types and gene targeting strategies have been suggested, the progress has been limited. Biological methods of influencing a patient's cardiac cells have been developed, some of which include administering biopharmaceutical compositions that affect cardiac pacing. Developments in genetic engineering have produced methods to make pacemaker-like cells from non-pacemaker cardiac cells or to regenerate the pacing capabilities of cells in the conduction system of the heart. For example, U.S. Pat. No. 6,214,620 describes a method for modulating the excitability of ventricular cells by controlling the regulation of the expression of certain ion channels (e.g. $K^+$ channels). WO 02/087419 and WO 05/062890 describe methods and systems for modulating electric behavior of cardiac cells by genetic modification of inwardly rectifying $K^+$ channels ($I_{K1}$) in quiescent ventricular cells.

Another biological approach for moderating cardiac pacing involves implanting into the SA node or other suitable heart regions cells having hyperpolarization-activated and cyclic nucleotide-gated (HCN) channels. For example, see WO 02/098286 and WO 05/062958A2. It is disclosed that, physiologically originating in the SA node, the HCN channels play a role in the control of rhythmic electrical heart activity. Cyclic nucleotides modulate the HCN channel activity, and channel activation occurs upon hyperpolarization rather than depolarization, generating an inward current, called "funny" current ($I_f$). There are four isoforms of HCN channels (HCN1-4), and each has greater or lesser prevalence in different heart regions. Because the HCN isoforms, generating the If current, are believed to be directly involved in generation and modulation of diastolic depolarization of cardiac pacemaker cells, implantation of HCN-expressing cells into cardiac tissue that is diseased or experiencing conduction blockage has been suggested as a viable method for regulating cardiac pacemaker function.

One group demonstrated that by injection of the adenylate cyclase VI gene into the heart ventricular muscle a biological cardiac pacemaker could be created (Ruhparwar A, et al., 2007, Scientific Sessions of the American Heart Association, Orlando, Fla.). Adenylyl cyclase 6 (AC6) is expressed in ventricular cells and is inhibited by $Ca^{2+}$. According to Ruhparwar et al., cyclic AMP (cAMP) is generated in response to β-adrenergic receptor (β-AR) stimulation and also binds to HCN channels, where it regulates spontaneous rhythmic activity in the heart. But targeting HCN channels cannot generate "funny" current ($I_f$) in adult ventricular myocytes because these cells do not express HCN channels and generate only a negligible $I_f$ current. There are two more major problems with this approach: absence of sustainability and absence of rhythmicity of spontaneous excitations. Previous studies showed that fast pacing in the presence of β-AR stimulation can indeed activate $Ca^{2+}$ cycling in ventricular myocytes, but this spontaneous activity is not sustained; it is only temporary, just a few beats, and cannot be rhythmic because it is associated with arrhythmogenic full-cell-length $Ca^{2+}$ waves. The $Ca^{2+}$ waves in ventricular or atrial myocytes are known to produce cardiac arrhythmia and therefore cannot provide a pacemaker function. Indeed, while each $Ca^{2+}$ wave generates its Delayed After-Depolarization (DAD), not every DAD results in the cell excitation. Spontaneous $Ca^{2+}$ waves and their DAD-induced excitations (if any) in cells with over-expression of β-ARs or $Ca^{2+}$ inhibitable AC6 do not occur under normal conditions but require extrinsic stimulation: electrical (fast pacing), nerve (to produce catecholamines), chemical, and/or hormonal (to activate β-ARs). Indeed, Ruhparwar et al. used rapid ventricular pacing combined with administration of isoprenaline (to activate β-ARs). The strong dependence on the extrinsic factors in cells with the $Ca^{2+}$ inhibited AC6 is not surprising, because the cAMP production is inhibited (and therefore not sustained) when the sarcoplasmic reticulum (SR) releases $Ca^{2+}$.

Another approach is to use in vitro-grown embryonic stem (ES) cell-derived cardiac cells (ESCs) as biological pacemakers. Since ESCs generate spontaneous action potentials (APs) and functionally integrate with ventricular myocytes in vitro and with the host mycocardium in vivo, they can pace hearts after their implantation (as reported in guinea pigs and pigs) and even overcome complete atrioventricular block in animal models. While these results show that these cells can potentially function as biological pacemakers, there are still some fundamental problems remaining with this approach.

One major problem is that ESCs are highly heterogeneous cells; they express major cardiac ion currents and $Ca^{2+}$ cycling proteins, but many ESCs generate irregular APs that could be proarrhythmic and, therefore, cannot be used in humans. Currently, there is no effective means to identify and select so called "sinus-node-like" cells generating rhythmic APs other than to directly measure those APs and/or chronotropic responses to neuromediators. While previous studies have suggested that several factors contributed to ESC automaticity, as shown in FIG. 1, such as interplay of $Ca^{2+}$ and $K^+$ currents, classical $I_f$ mechanism and $I_{CaT}$, $I_{Na}$ window current, global $Ca^{2+}$ oscillations activating a nonselective cation current, and different types of local $Ca^{2+}$ releases (LCRs) from SR, their complex interactions and roles to generate spontaneous Aps are unknown. The requirements for ESCs to generate rhythmic APs also remain unknown.

The complex nature of cardiac pacemaker function and regulation has been the subject of debate and intensive experimental studies. It has been widely believed that the $I_f$ current, sometimes called "the pacemaker current", is the dominant mechanism of cardiac pacemaker function and the heart rate regulation. More recent studies in genetically manipulated mice demonstrated, however, that the cardiac pacemaker function and heart response to β-AR stimulation are preserved in the absence of $I_f$ or in the absence of cAMP sensitivity of $I_f$. Alternatively, based on previous studies in cardiac Purkinje cells, pacemaker oscillations were described to be the resultant of a surface membrane oscillator and a subcellular rhythm generator, which is largely independent from the surface membrane. The strongly coupled function of $Ca^{2+}$ and membrane oscillators/clocks in the heart's natural pacemaker, sinoatrial node is now emerging as a novel fundamental principle of cardiac impulse initiation and regulation (Lakatta E G, et al., 2010 Circ Res 106: 659-673).

What is needed are biological pacemakers engineered to intrinsically generate excitations which, similar to those of natural pacemakers, must be rhythmic and sustained for many years, in the best case for the rest of the patient's life.

SUMMARY OF THE INVENTION

One aspect of the invention is a method of producing a biological pacemaker, comprising: providing a plurality of electrically excitable cells; and increasing the level of intracellular cAMP, increasing PKA activity, or increasing CaMK II activity in said plurality of electrically excitable cells by administering a gene that expresses a regulatory protein that modulates cAMP levels and/or CaMK II activity in said plurality of electrically excitable cells. An embodiment is the method, wherein said electrically excitable cells are cardiac cells derived in vitro from embryonic stems cells, mesenchymal stem cells, or iPS cells. Another embodiment is the method, wherein said regulatory protein is an adenylyl cyclase, a phosphodiesterase, calcium/calmodulin-dependent protein kinase II, or a combination thereof; preferably the adenylyl cyclase is a constitutively active $Ca^{2+}$-activated adenylyl cyclase type 1, $Ca^{2+}$-activated adenylyl cyclase type 8, or a combination thereof.

Another aspect of the invention is a method of producing spontaneous rhythmic excitation in electrically excitable cells, comprising: providing a plurality of said electrically excitable cells; and increasing the level of intracellular cAMP, increasing PKA activity, or increasing CaMK II activity in said plurality of said electrically excitable cells by administration a gene that expresses a regulatory protein that modulates intracellular cAMP, PKA activity, or CaMK II activity in said plurality of said electrically excitable cells. An embodiment is the method, wherein said electrically excitable cells are cardiac cells derived in vitro from embryonic stems cells, mesenchymal stem cells, or iPS cells. Another embodiment is the method, wherein said regulatory protein is an adenylyl cyclase, a phosphodiesterase, calcium/calmodulin-dependent protein kinase II, or a combination thereof; preferably the adenylyl cyclase is a constitutively active $Ca^{2+}$-activated adenylyl cyclase type 1, $Ca^{2+}$-activated adenylyl cyclase type 8, or a combination thereof.

Another aspect of the invention is method of producing a biological pacemaker, comprising: providing a plurality of electrically excitable cells; increasing the level of intracellular cAMP, increasing PICA activity, or increasing CaMK II activity in said plurality of electrically excitable cells; and modulating at least one $Ca^{2+}$ clock and at least one membrane clock in said electrically excitable cells, wherein said modulation of said at least one $Ca^{2+}$ clock and said at least one membrane clock increases the level of intracellular cAMP levels, PKA activity, or CaMK II activity. An embodiment is the method, wherein said modulation comprises a step of administering a gene that expresses a regulatory protein that modulates cAMP levels, PKA activity, or CaMK II activity into said electrically excitable cells. An embodiment is the method, wherein said electrically excitable cells are cardiac cells derived in vitro from embryonic stems cells, mesenchymal stem cells, or iPS cells. Another embodiment is the method, wherein said regulatory protein is an adenylyl cyclase, a phosphodiesterase, calcium/calmodulin-dependent protein kinase II, or a combination thereof; preferably the adenylyl cyclase is a constitutively active $Ca^{2+}$-activated adenylyl cyclase type 1, $Ca^{2+}$-activated adenylyl cyclase type 8, or a combination thereof.

Another aspect of the invention is a method of producing a biological pacemaker, comprising: providing a plurality of electrically excitable cells; and sustainably increasing the level of intracellular cAMP, increasing PKA activity, or increasing CaMK II activity in said plurality of electrically excitable cells.

Another aspect of the invention is a biological pacemaker, comprising: a plurality of cardiac cells; wherein said plurality of cardiac cells are derived in vitro from embryonic stems cells or mesenchymal stem cells; and wherein the level of intracellular cAMP, increasing PKA activity, or increasing CaMK II activity in said plurality of cardiac cells is maintained at an elevated level relative to constitutive cardiac cells to provide sustained rhythmic spontaneous excitations of said cardiac cells.

Another aspect of the invention is a biological pacemaker prepared by any of the methods, above.

Another aspect of the invention is a method of treating or preventing arrhythmia in a patient, comprising: preparing a biological pacemaker using any of the above methods; and administering said biological pacemaker into the heart of said patient in need thereof.

Another aspect of the invention is a method of treating or preventing heart disease associated with a defective pacemaker in a patient, comprising: preparing a biological pacemaker by any of the above methods; and administering said biological pacemaker into the heart of said patient in need thereof.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
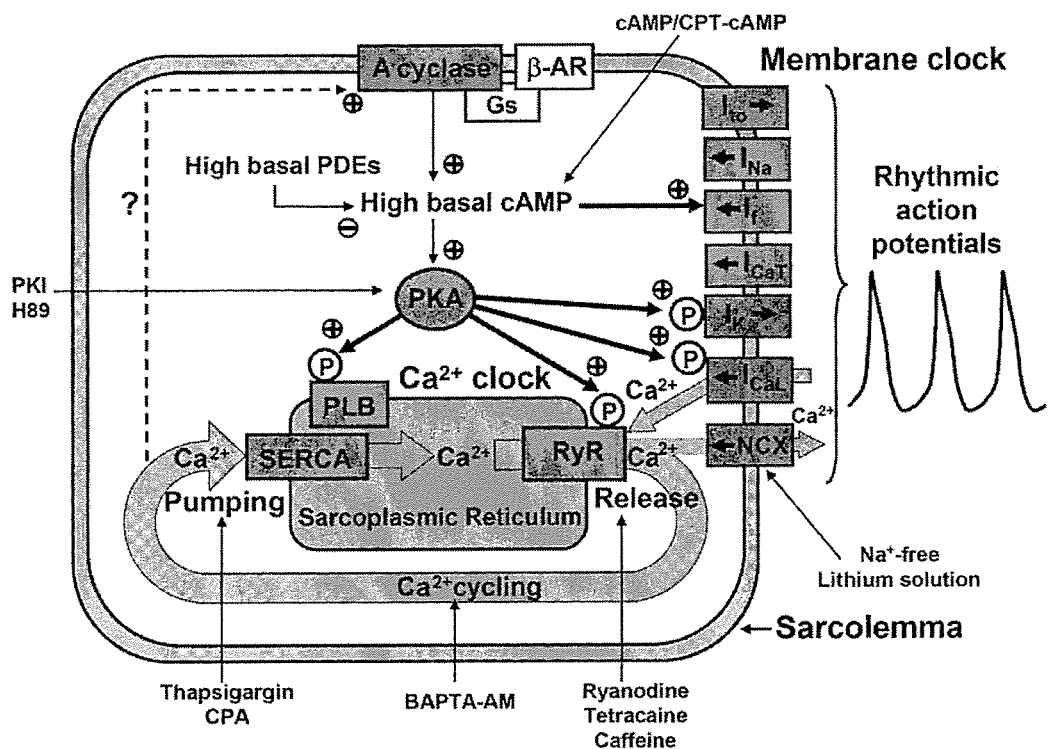
FIG. 1 is a schematic representation of the integration of intracellular ($Ca^{2+}$ clock) and sarcolemmal (membrane clock) processes in ESCs to function as rhythmic pacemakers. Also shown are pharmacological tools used in study described in the examples to target specific components of the integrative pacemaker mechanism.

Applicants describe herein how the integrated function of SR and sarcolemma in ESCs generate spontaneous rhythmic and sustained APs. Experimental evidence presented herein indicate that the rhythmic operation of these in vitro-derived cells as putative biological pacemakers is based on strongly and dynamically coupled function of intracellular $Ca^{2+}$ cycling and membrane current activation (FIG. 1). The automaticity of ESCs is complex and includes entrainment of $Ca^{2+}$ clock and membrane clock. This mechanism of automaticity is fundamentally different than those previously suggested for ESCs. Applicants show herein that this mechanism also underlies rhythmic automaticity of ESCs.

The invention is directed, in part, to molecular targets ("coupling factors") that regulate function of proteins of both clocks ($Ca^{2+}$ clock and membrane clock) in natural pacemakers and their use in methods to produce spontaneous rhythmic excitations of electrically excitable cells capable of functioning as biological pacemakers, including, but not limited to, cardiac cells or cardiac-like cells derived from embryonic stem cells or mesenchymal stem cells, or iPS cells. In certain embodiments, the coupling factors are regulatory proteins capable of modulating (increasing) the level of intracellular cAMP and/or PKA activity and/or CaMK II activity, which, in turn, enhances coupling of $Ca^{2+}$ clock and membrane clock and thereby converts irregularly and/or rarely spontaneously active cells into highly-performing cell pacemakers generating rhythmic, frequent, and sustained excitations.

Applicants showed the integrative mechanism of rhythmic ESC automaticity and discovered that late-stage ESCs exhibit both the membrane clock (the ensemble of sarcolemmal, time- and voltage-dependent ion currents, generating APs) and rhythmic local $Ca^{2+}$ releases (LCRs), i.e., local $Ca^{2+}$ oscillators or $Ca^{2+}$ clocks. Applicants found that SR $Ca^{2+}$ loading and rhythmic LCRs in ESCs are driven by a high basal activity of the cAMP-dependent PKA and dynamically interact with the membrane clock via activation of L-type $Ca^{2+}$ current ($I_{CaL}$) and NCX. Applicants' results thus indicated that in contrast to previously suggested simple mechanisms (driven by either $Ca^{2+}$ releases or membrane channels), the actual mechanism of rhythmic ESC automaticity is complex, as shown in FIG. 1, and the enhanced, cAMP/PKA-driven functionality of both $Ca^{2+}$ clock and membrane clock and their strong two-way dynamic coupling are crucial factors for ESC to function as robust biological pacemakers that must generate rhythmic and sustained excitations.

The present invention relates to the biological pacemaker of the invention that generates rhythmic excitations by its own intrinsic, built-in mechanism (two interacting clocks). The design of the biological pacemaker of the invention follows the design of natural pacemakers A coupled SYSTEM of intracellular $Ca^{2+}$ clocks and surface membrane voltage clocks controls the timekeeping mechanism of the heart's pacemaker. *Circ Res* 106: 659-673, 2010). The $Ca^{2+}$-activated adenylyl cyclase 1 (AC1) and/or adenylyl cyclase 8 (AC8) (both expressed in pacemaker cells, driving their pacemaker function, and mediating heart rate regulation) are targeted, rather than $Ca^{2+}$-inhibited adenylyl cyclase 6 (expressed and functioning in ventricular muscle cells to increase heart contractility). While not wishing to be bound by theory, it is believed that enhancing $Ca^{2+}$ activated AC1 and AC8 is critical in intrinsic pacemaker mechanism of the invention in order to close the positive feed-back enzymatic loop:

Ca_activ.AC1&8→cAMP→PKA→PLB&RyR&$I_{CaL}$→ moreCa→Ca_activ.ACs1&8 that sustains both high basal cAMP and SR $Ca^{2+}$ oscillations ($Ca^{2+}$ clock) driving rhythmic excitations in cardiac pacemaker cells via activation of the diastolic inward NCX current. Spontaneous excitations (if any) in myocardial cells with over-expression of β-ARs or $Ca^{2+}$ inhibited AC6 do not occur under normal conditions but require extrinsic stimulation: electrical (fast pacing), nerve (to produce catecholamines), chemical, and/or hormonal (to activate β-ARs). Indeed, Ruhparwar et al. used rapid ventricular pacing combined with administration of isoprenaline (to activate β-ARs). The strong dependence on the extrinsic factors in cells with the $Ca^{2+}$ inhibited AC6 is not surprising, because the cAMP production is inhibited (and not sustained) when SR releases $Ca^{2+}$. Another alternative or complementary way to close the positive feed-back enzymatic loop resulting in sustained and rhythmic excitable cell automaticity is to enhance CaMK II signaling, another strong coupling factor of natural pacemaker cells:

CaMK II→PLB&SERCA&RyR&$I_{CaL}$→moreCa→ Calmodulin→CaMK II.

Indeed, CaMK II phoSphorylates multiple proteins (e.g. PLB, SERCA, RyR, and L-type $Ca^{2+}$ channels) of both $Ca^{2+}$ clock in membrane clock resulting in the enhanced function of both clocks and their stronger coupling in pacemaker cells. Previous studies showed that CaMK II activity is required for both basal function and autonomic regulation of sinoatrial node cells (e.g. Vinogradova et al. 2000. Circ Res 87:760-767; and Wu et al. 2009, Proc Natl Acad Sci USA 106:5972-5977).

The in vitro-grown pacemaker cells of the invention have a harmonized balance of all critical components of both $Ca^{2+}$ and membrane interacting clocks required for normal pacemaker function. In the mechanism of the invention, $Ca^{2+}$ clock generates rhythmic, strongly synchronized $Ca^{2+}$ wavelets, i.e. LCRs, which ignite rhythmic APs via activation of the diastolic inward NCX current. Each cycle the cell looses $Ca^{2+}$ via NCX, but $I_{CaL}$ during each AP provides $Ca^{2+}$ influx that compensates the loss so that the system reaches a steady-state balance of intracellular $Ca^{2+}$. Thus, as a result of sustained elevated levels of intracellular cAMP and/or PKA activity and/or CaMK II activity, the two clocks of pacemaker cells ($Ca^{2+}$ clock and membrane clock) become functionally coupled and permanent biological pacemakers may thereby be engineered.

As employed above and throughout the disclosure, the following terms, unless otherwise indicated, shall be understood to have the following meanings.

As used herein, the singular forms "a," "an," and "the" include the plural reference unless the context clearly indicates otherwise.

As used herein, the term "about," when referring to a measurable value such as an amount, a temporal duration, and the like, is meant to encompass variations off 20%, preferably ±10%, more preferably ±5%, even more preferably ±1%, and yet even more preferably ±0.1% from the specified value, as such variations are appropriate to perform the disclosed methods.

As used herein, "patient" refers to animals, including mammals, preferably humans.

As used herein, "electrically excitable cell" refers to cells that are capable of generating electrical excitations, electrical impulses, or action potentials of their surface membrane but either not spontaneously active or substantially lack rhythmicity of spontaneous excitations, including, but not limited to adult cells, embryonic cells, and cells derived from stem cells (such as embryonic stem cells, mesenchymal stem cells, and induced stem cells, including iPS cells). An electrically excitable cell may be produced by techniques known to those skilled in the art. Electrically excitable cells may be created from electrically neutral cells, like fibroblasts, by expression of a proper set of voltage-gated ion channels. Electrically excitable cells of the body include, for example, a variety of cardiac cells, skeletal muscle cells, smooth muscle cells, and neurons. Stem cell-derived cardiac cells (grown and differentiated in vitro) are another example of an electrically excitable cell that is suitable for the various embodiments of the invention.

As used herein, "stem cell" refers to any cell having the potential to differentiate into one or more different cell types. Such cells include, but are not limited to, stem cells derived from a variety of different sources including, for example, bone marrow, embryonic blastocysts or yolk sac, spleen, blood, including peripheral blood and umbilical cord blood, adipose tissue and other tissues and organs. Such stem cells include, but are not limited to, hematopoietic stem cells, endothelial progenitor cells, any induced stem cells (including iPS cells), or embryonic stem cells.

As used herein, embryonic stem cells (ES cells) refers to embryonic pluripotent stem cells that can differentiate into a variety of cell types.

As used herein, mesenchymal stem cells (MSCs) refers to multipotent stem cells that can differentiate into a variety of cell types.

Stem cells may be obtained from a variety of different donor sources. In a preferred embodiment, autologous stem cells are obtained from the subject who is to receive the transplanted stem cells to avoid immunological rejection of foreign tissue. In yet another preferred embodiment of the invention, allogenic stem cells may be obtained from donors who are genetically related to the recipient and share the same transplantation antigens on the surface of their stem cells. Alternatively, stem cells may be derived from antigenically matched (identified through a national registry) donors. In instances where antigenically matched stem cells cannot be located, non-matched cells may be used; however, it may be necessary to administer immunosuppressive agents to prevent recipient rejection of the donor stem cells.

Procedures for harvest and isolation of such stem cells are well known to those of skill in the art and do not differ from those used in conventional stem cell isolation. Adult stem cells, including any induced stem cells and iPS cells, may be derived from, but not limited to, bone marrow, peripheral blood, adipose tissue and other adult tissues and organs. For derivation of embryonic stem cells, stem cells can be extracted from the embryonic inner cell mass during the blastocyst stage. Fetal stem cells may be derived from the liver, spleen, brain, or heart of fetuses, 4-12 weeks gestation, following elective abortions, terminated ectopic pregnancies, or spontaneous miscarriages.

In a non-limiting embodiment of the invention, antibodies that bind to cell surface markers selectively expressed on the surface of stem cells may be used to identify or enrich for populations of stem cells using a variety of methods. Such markers include, for example, CD34, SSEA3, SSEA4, anti-TRA1-60, anti-TRA1-81, or c-kit.

In an embodiment of the invention, MSCs may be derived from bone marrow aspirates. For example, 10 ml of marrow aspirate is collected into a syringe containing 6000 units of heparin to prevent clotting, washed twice in phosphate buffer solution (PBS), added to 20 ml of control medium (DMEM containing 10% FBS), and then centrifuged to pellet the cells and remove the fat. The cell pellet is then resuspended in control medium and fractionated at 1100 g for 30 minutes on a density gradient generated by centrifugation of a 70% percoll solution at 13000 g for 20 minutes. The MSC-enriched, low density fraction is collected, rinsed with control medium, and plate d at a density of $10^7$ nucleated cells per 60 mm$^2$ dish. Alternatively, MSCs (POIETICS® hMSCs) to be used in the practice of the invention can be purchased from Clonetics/Bio Whittaker (Walkersville, Md.).

In a specific embodiment of the invention, MSCs are grown on polystyrene tissue culture dishes and maintained at 37° C. in humidified 5% $CO_2$ in Mesenchymal Stem Cell Growth Media supplemented with L-glutamine, penicillin and serum (MSCGM BulletKit, Cambrex). Cells are re-plated for passaging once every two weeks. The MSCs are then cultured in control medium at 37° C. in a humidified atmosphere containing 5% $CO_2$.

The biological pacemaker cells may be genetically engineered to express one or more genes encoding a regulatory protein that modulates cAMP levels or activity of PKA or CaMK II. Such engineered cells are described in detailed below. The cells may be genetically engineered using techniques well known in the art to express proteins that further enhance the ability of such cells to provide biological pacemaker activity. Such techniques include, for example, in vitro recombinant DNA techniques, synthetic techniques, and in vivo genetic recombination. (See, for example, the techniques described in Sambrook J., et al. 2000. Molecular Cloning: A Laboratory Manual (Third Edition), and Ausubel, et al. (1996) Current Protocols in Molecular Biology John Wiley and Sons Inc., USA). Any of the methods available in the art for gene delivery into a host cell can be used according to the present invention to deliver genes into the target cell population. Such methods include electroporation, lipofection, calcium phosphate mediated transfection, or viral infection. For general reviews of the methods of gene delivery see Strauss, M. and Barranger, J. A., 1997, *Concepts in Gene Therapy*, by Walter de Gruyter & Co., Berlin; Goldspiel, et al., 1993, *Clinical Pharmacy* 12:488-505; Wu and Wu, 1991, Biotherapy 3:87-95; Tolstoshev, 1993, *Ann. Rev. Pharmacol. Toxicol.* 33:573-596; Mulligan, 1993, Science 260:926-932; and Morgan and Anderson, 1993, *Ann. Rev. Biochem.* 62:191-217; 1993, TIBTECH 11(5):155-215.

The polynucleotides of the gene that expresses CaMK II or a regulatory protein that modulates cAMP levels or activity of PKA or CaMK II can be made by traditional PCR-based amplification and known cloning techniques. Alternatively, a polynucleotide of the invention can be made by automated procedures that are well known in the art. The polynucleotides of the gene should include a start codon to initiate transcription and a stop codon to terminate translation. Suitable polynucleotides for use with the invention can be obtained from a variety of public sources including, without limitation, GenBank (National Center for Biotechnology Information (NCBI)), EMBL data library, SWISS-PROT (University of Geneva, Switzerland), the PIR-International database; and the American Type Culture Collection (ATCC) (10801 University Boulevard, Manassas, Va. 20110-2209). See generally, Benson, D. A. et al, Nucl. Acids. Res., 25:1 (1997) for a description of GenBank. The particular polynucleotides useful with the present invention are readily obtained by accessing public information from GenBank.

Any suitable DNA vector or delivery vehicle may be utilized to transfer the desired nucleotide sequence to the targeted cells. For example, the nucleotide sequence may be cloned into a viral vector such as an adenoviral associated vector (AAV) or other viral vectors such as herpes vectors, and retroviral vectors such as lentiviral vectors. The type of viral vector selected is dependent on the target tissue and the length of the sequence to be delivered. For a discussion of viral vectors see Gene Transfer and Expression Protocols, Murray ed., pp. 109-206 (1991). Alternatively, non-viral delivery systems may be utilized. For example, liposome: DNA complexes, plasmid:liposome complexes, naked DNA, DNA-coated particles, or polymer based systems may be used to deliver the desired sequence to the targeted cardiac cells. The above-mentioned delivery systems and protocols therefore are described in *Gene Targeting Protocols*, Kmeic 2ed. pp. 1-35 (2002), and *Gene Transfer and Expression Protocols*, Vol. 7, Murray ed. pp 81-89 (1991).

AAV vectors can be constructed using techniques well known in the art. Typically, the vector is constructed so as to provide operatively linked components of control elements. For example, a typical vector includes a transcriptional initiation region, a nucleotide sequence of the protein to be expressed, and a transcriptional termination region. Typically, such an operatively linked construct will be flanked at its 5' and 3' regions with AAV ITR sequences, which are required viral cis elements. The control sequences can often be provided from promoters derived from viruses such as, polyoma, Adenovirus 2, cytomegalovirus, and Simian Virus 40. Viral regulatory sequences can be selected to achieve a high level of expression in a variety of cells. Alternatively, ubiquitously expressing promoters, such as the early cytomegalovirus promoter can be utilized to accomplish expression in any cell type. A third alternative is the use of promoters that drive tissue specific expression. This approach is particularly useful where expression of the desired protein in non-target tissue may have deleterious effects. Thus, according to another preferred embodiment, the vector contains the proximal human brain natriuretic peptide (hBNP) promoter that functions as a cardiac-specific promoter. For details on construction of such a vector see LaPointe et al., 2002, *Am. J. Physiol. Heart Circ. Physiol.*, 283:H1439-45.

Vectors may also contain cardiac enhancers to increase the expression of the transgene in the targeted regions of the cardiac conduction system. Such enhancer elements may include the cardiac specific enhancer elements derived from Csx/Nkx2.5 regulatory regions disclosed in the published US-A-20020022259, the teachings of which are herein incorporated by reference.

Therapeutic methods of the present invention include delivery of an effective amount of a genetic construct or genetically engineered cells or unmodified cells with pacemaking activity to the cardiac cells to produce a biological pacemaker that improve/enhance the rate and rhythm of the intrinsic pacing activity of such cells. As described above, the engineered biological pacemakers may be introduced using genetically engineered vectors, genetically engineered cells, or unmodified cells, which are implanted at a selected location. One delivery method includes the use of a delivery tool, such as a catheter having electric sensing capabilities, which is introduced directly into either the right atrium or the right ventricle, as just a couple of examples. The delivery tool may include electrodes for sensing electric activity and delivering pacing stimuli in order to determine the desired location for the biological pacemakers. Once the location is determined, genetically engineered viruses, gene-modified cells, or unmodified cells are delivered to the myocardium at that location to form a biological pacemaker. The delivery tool may include an injection device that injects the viruses or cells into the desired/targeted cardiac tissues, including the myocardium, the cardiac conduction tissues, or the sinoatrial node, the primary cardiac pacemaker. One suitable method for injecting a genetic construct directly into the myocardium is described by R. J. Guzman et al., *Circ. Res.*, 73:1202-1207 (1993). Furthermore, a delivery system for delivering genetic material to a targeted heart region is described in U.S. Pat. No. 7,103,418 and WO 98/02150, the teachings of which are incorporated herein by reference. Alternatively; genetically engineered cells may be cultured and proliferated on a solid scaffold, and then surgically delivered to the selected heart region together with the scaffold. The scaffold may also be directly injected into the targeted cardiac tissue.

Perfusion protocols that are useful with the inventive methods are often sufficiently capable of delivering a genetic construct to at least about 10% of cardiac myocytes. Infusion volumes of between about 0.01 ml and about 1 ml are useful for direct intramyocardial injection. Also, suitable methods for targeting non-viral vector genetic constructs to the heart are described in U.S. Pat. No. 6,376,471, the teachings of which are hereby incorporated by reference.

When a genetic construct (in contrast to genetically engineered cells or unmodified cells) is introduced to the targeted heart tissue using any suitable technique, the genetic material is delivered into the cells by, for example, transfection or transduction procedures. Transfection and transduction refer to the acquisition by a cell of new genetic material by incorporation of added nucleic acid molecules. Transfection can occur by physical or chemical methods. Many transfection techniques are known to those of ordinary skill in the art including, without limitation, calcium phosphate DNA co-precipitation, DEAE-dextrin DNA transfection, electroporation, naked plasmid adsorption, and cationic liposome-mediated transfection (commonly known as lipofection). Transduction refers to the process of transferring nucleic acid into a cell using a DNA or RNA virus. Suitable viral vectors for use as transducing agents include, but are not limited to, retroviral vectors, adeno-associated viral vectors, lentiviral vectors, herpes simplex viral vectors, vaccinia viruses, and Semliki Foret virus vectors.

Depending on the type of biological pacemaker and the heart condition, it may take from days to weeks after implantation before transfected or genetically engineered cells express their pacing functions.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system, or process.

Accordingly, the invention is directed to molecular targets ("coupling factors") that regulate function of proteins of both clocks ($Ca^{2+}$ clock and membrane clock) in natural pacemakers and their use in methods to produce spontaneous rhythmic excitation of cardiomyocytes capable of functioning as a biological pacemaker, including, but not limited to, cardiac cells derived from embryonic stem cells or mesenchymal stem cells or iPS cells. In certain embodiments, the coupling factors are regulatory proteins capable of modulating (increasing) the level of intracellular cAMP and/or PKA activity and/or CaMK II activity, which in turn converts irregularly and/or rarely spontaneously active cells into highly-performing cell pacemakers spontaneously generating rhythmic, frequent, and sustained excitations.

Heart diseases associated with a defective pacemaker that may be treated using the engineered biological pacemakers of the invention including, for example, pathological arrhythmia, conduction block, complete atrioventricular block, incomplete atrioventricular block, bundle branch block, sinus node dysfunction, sinus bradycardia, marginal or weak pacemaker activity, sick sinus syndrome, tachyarrhythmia, sinus node reentry tachycardia, atrial tachycardia from an ectopic focus, atrial flutter, atrial fibrillation, bradyarrhythmia, or cardiac failure. In certain embodiments, the engineered biological pacemaker is administered to the left or right atrial muscle, sinoatrial node, or atrioventricular junctional region of the patient's heart.

Further, the biological pacemaker may be provided to the Bachman's bundle, sinoatrial node, atrioventricular junctional region, H is branch, left or right bundle branch, Purkinke fibers, right or left atrial muscle or ventricular muscle of the patient's heart. In certain embodiment, a pre-existing source of pacemaker activity in the heart may be ablated.

As used herein, the term "administering" shall mean delivering in a manner which is affected or performed using any of the various methods and delivery systems known to those skilled in the art. Administering can be performed, for example, pericardially, intracardially, subepicardially, transendocardially, via implant, via catheter, intracoronarily, intravenously, intramuscularly, subcutaneously, parenterally, topically, orally, transmucosally, transdermally, intradermally, intraperitoneally, intrathecally, intralymphatically, intralesionally, epidurally, or by in vivo electroporation. Administering can also be performed, for example, once, a plurality of times, and/or over one or more extended periods.

The engineered biological pacemakers may require focal delivery. Several methods to achieve focal delivery are feasible; for example, the use of catheters and needles, and/or growth on a matrix and a "glue." Whatever approach is selected, methods and compositions of the present invention provide a means for determining whether the delivered cells disperse from the target site. Such dispersion could introduce unwanted electrical effects within the heart or in other organs.

The present invention further relates to pharmaceutical compositions comprising biological pacemaker cells and a pharmaceutically acceptable carrier. Pharmaceutically acceptable carriers are well known to those skilled in the art and include, but are not limited to, 0.01-0.1 M and preferably 0.05 M phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions, or suspensions, saline and buffered media. Examples of non-aqueous solvents are propylene glycol, polyethylene glycol, vegetable oils such as olive oil, and injectable organic esters such as ethyl oleate. Preservatives and other additives, such as, for example, antimicrobials, antioxidants, and chelating agents may also be included with all the above carriers.

As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. The composition can be formulated as a suppository, with traditional binders and carriers such as triglycerides. Oral formulation can include standard carvers such as pharmaceutical grades of mannitol, lactose, starch, magnesium stearate, sodium saccharine, cellulose, magnesium carbonate, and the like. Examples of suitable pharmaceutical carriers are described in "Remington's Pharmaceutical Sciences" by E. W. Martin. Such compositions will contain a therapeutically effective amount of the therapeutic compound, preferably in purified form, together with a suitable amount of carrier so as to provide the form for proper administration to the patient. The formulation should suit the mode of administration.

The appropriate concentration of the regulatory protein and/or composition of the invention which will be effective in the treatment of a particular heart disease associated with a defective pacemaker disorder or condition will depend on the nature of the disorder or condition, and can be determined by one of skill in the art using standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose response curves derived from in vitro or animal model test systems. Additionally, the administration of the compound could be combined with other known efficacious drugs if the in vitro and in vivo studies indicate a synergistic or additive therapeutic effect when administered in combination.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods, and examples are illustrative only and not limiting.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Culture and Differentiation of ES Cells

Only late-stage differentiated ESCs (7+9 to 14 days) were used. These cells possess both major ion channels ($I_{CaL}$, $I_f$, $I_{Na}$, $I_{to}$, $I_K$)(4), exchangers (NCX), and $Ca^{2+}$ cycling proteins (RyR2, SERCA2A, calcequestrin, and phospholamban). Late-stage ESCs have been successfully used as temporary biological pacemakers in whole animal model experiments.

Mouse ES cells of line R1 were differentiated into cardiac cells using the "hanging drop" technique. ESCs were isolated from in vitro-grown embryoid bodies by microdissection followed by collagenase treatment. ES cells of line R1 were cultivated on inactivated feeder layer of primary mouse embryonic fibroblasts on gelatin (0.1%)-coated petri dishes (Fischerbrand) in DMEM supplemented with 15% heat-inactivated fetal bovine serum (FBS), 2 mmol/L L-glutamine, 0.1 mmol/L γ-mercaptoethanol, non-essential amino acids (NEAA, stock solution diluted 1:100), penicillin-streptomycin (stock solution diluted 1:100) and 10 ng/ml LIF. For spontaneous differentiation, ES cells (n=400) were induced to form embryoid bodies (EBs) in hanging drops (1) with DMEM supplemented with 15% FBS, L-glutamine, non-essential amino acids and penicillin-streptomycin. At day 2, EBs were transferred into bacteriological petri dishes and cultured in suspension until day 5. At day 7, EBs were plated onto gelatin-coated 6 cm tissue culture dishes (Fischerbrand) and cultivated in DMEM supplemented with 15% FBS, L-glutamine, NEAA and penicillin-streptomycin. Individual spontaneously beating ESCs were isolated by microdissection and collagenase treatment.

Example 2

Electrophysiology

ESCs differentiated in vitro for 9 to 20 days after plating of 7 days old embryoid bodies were studied during continuous superfusion with solution containing in mmol/L: 140 NaCl, 5.4 KCl, 5 HEPES, 2 $MgCl_2$, 1.8 $CaCl_2$, 10 glucose, (pH adjusted to 7.4 with NaOH). Selection of the cells for patch-clamp technique was based on spontaneous beating. Action potentials were measured at physiological temperature (35±2° C.) with standard current-clamp technique (Axopatch 200, Axon Instruments, Foster City, Calif., USA), pCLAMP7 software was used for data acquisition and analysis (Axon Instruments). Perforated patch-clamp technique was performed with β-escin added to the electrode solution. Patch pipette solution contained in mmol/L: 120 K-gluconate, 5 NaCl, 5 Mg-ATP, 5 HEPES, 20 KCl, 3 $Na_2ATP$ (pH adjusted to 7.2 with NaOH). Recording of L-type $Ca^{2+}$ current ($I_{CaL}$) simultaneously with $Ca^{2+}$ signal imaging (see Example 3) were performed under whole cell voltage clamp. Patch pipette filling solution contained (in mmol/L) 120 CsCl, 10 NaCl, 20 tetraethylammonium chloride, 5 MgATP, and 20 HEPES (pH 7.2 adjusted with CsOH), and 100 μmol/L fluo-4 pentapotassium salt (Molecular Probes). Four conditioning pulses of 100 ms and 0 mV were delivered at 1.0 Hz prior to each test voltage pulse to load the SR with $Ca^{2+}$.

Example 3

$Ca^{2+}$ Imaging in Intact Cells

Confocal imaging of $Ca^{2+}$ release in ESCs was performed by placing cells on the stage of a inverted confocal microscope and loaded for 15 min with 10 μmol/L fluo-4 AM in dimethyl sulfoxide (Molecular Probes, Eugene, Oreg.) in perforated patch experiments. In whole cell configuration, fluo-4 was added directly to the pipette solution.

Example 4

Chemical Skinning of ESCs and $Ca^{2+}$ Imaging of the Skinned Cells

ESCs were plated in differentiation medium on 35 mm thin (0-type) glass-bottom petri dishes from MatTek Corporation. The heater lens heated the bottom of the chamber and pre-heater was used for perfusion of the chamber; temperature was controlled by Analog TC2BIP 2/3Ch Bipolar Temp controller from CellMicroControls. Only beating ESCs were permeabilized with saponin (0.01%) added to "intracellular" solution containing (mmol/L): 100 potassium aspartate, 10 NaCl, 3 MgATP (free $[Mg^{2+}]$ ~1 mol/L), 0.5 EGTA, 10 phosphocreatine, 5 U $ml^{-1}$ creatine phosphokinase, pH 7.2. After 60 s of permeabilization and washing out of saponin, "intracellular" solution containing Fluo-4 pentapotassium salt (30 mmol/L) was added. Free $[Ca^{2+}]$ was calculated (at given total concentrations of $Ca^{2+}$, $Mg^{2+}$, ATP and EGTA) using a computer program (WinMAXC 2.50, Stanford University, CA, USA) and amounts to ~60-80 nM or 150 nM in some experiments. Spontaneous LCRs and SR $Ca^{2+}$ load estimated by line-scanning confocal microscopy at 35° C. Excitation was a 488 nm line of an argon ion laser for excitation of Fluo-4. The fluorescence was recorded at wavelengths>515. The SR $Ca^{2+}$ load, indexed as $Ca^{2+}$ released by a rapid application of caffeine, was assessed by a confocal line scan image as the amplitude of Fluo-4 of $Ca^{2+}$ fluorescent transient ($F/F_o$).

Example 5

Image Analysis

Fluo-4 measurements are presented in terms of $F/F_0$ (normalized $Ca^{2+}$ signal). Images were and action potentials were analyzed by programs developed using Delfi-7 software. The duration and width of LCRs were measured as the time at half-maximal amplitude of the normalized signal.

Example 6

Figure 2:
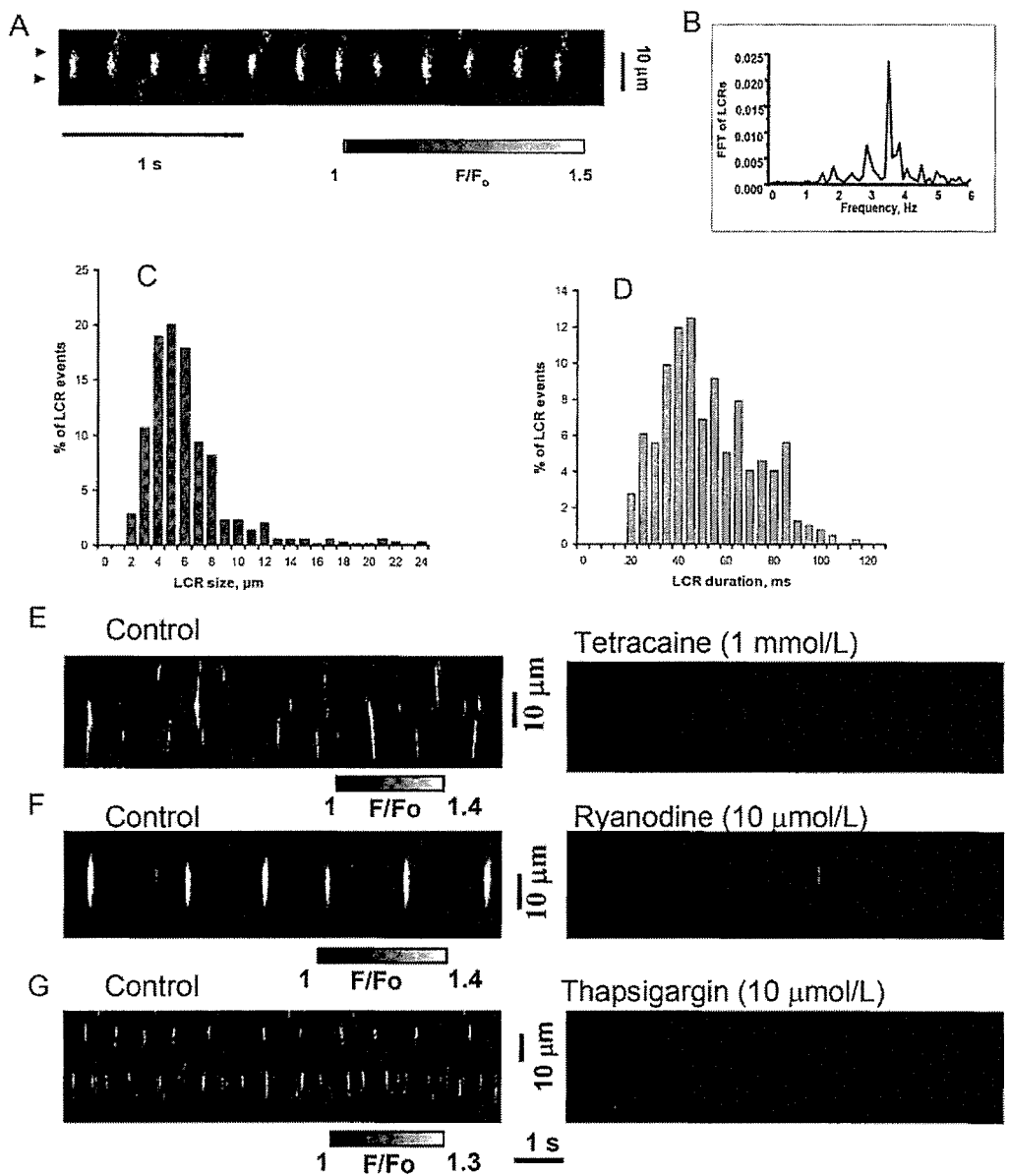
FIG. 2 shows local $Ca^{2+}$ releases (LCRs) in saponin-skinned ESCs are rhythmic and linked to SR function (RyRs and SERCA). Panel A is a confocal line-scan image of $Ca^{2+}$ signals in a representative ESC. Panel B is a Fast Fourier transform (FFT) of a continuous 27 second long recording of LCRs (for the average signal in a cell fragment between triangles in panel A). Panels C and D are histograms of LCR size, indexed as the full width at half maximum amplitude (FWHM) and duration, characterized as the full duration at half-maximum amplitude (FDHM) (747 LCRs, 17 cells). Panels E to G are confocal line-scan images of representative ESCs before (left) and after (right) superfusion with 10 µmol/L ryanodine, 1 mmol/L tetracaine, 10 µmol/L thapsigargin. Cells were bathed in 150 nmol/L free $[Ca^{2+}]$.

Characterization of $Ca^{2+}$ Clock in Chemically Skinned and Voltage-Clamped ESCs The major distinctive property of the $Ca^{2+}$ clock in natural pacemakers is its ability to produce spontaneously rhythmic LCRs independently on membrane function in chemically skinned or voltage-clamped cells, when activation of ion channels is disabled. Chemically skinned ESCs produced wavelet-like LCRs at a low bathing $[Ca^{2+}]$ of 150 nmol/L (FIG. 2, Panel A). Those LCRs are rhythmic with a dominant frequency ranging from 1 to 6.5 Hz (3.9+/−0.5 z, n=10 cells) as illustrated by Fast Fourier transform (FFT) (FIG. 2, Panel B). The LCRs width range from 1.8 to 22 μm (5.58±0.12 μm, 747 LCRs, 17 cells) in size and from 20 to 110 ms in duration (49.2±0.9 ms) (FIG. 2, Panels C and D). The LCRs are likely produced by ryanodine receptors (RyRs) from the SR as they are inhibited by disabling of either this SR $Ca^{2+}$ release channel (by 10 μmol/L ryanodine or 1 mmol/L tetracaine) or SR $Ca^{2+}$ pump (by 10 μmol/L thapsigargin (see FIG. 2, Panels E to G).

Figure 3:
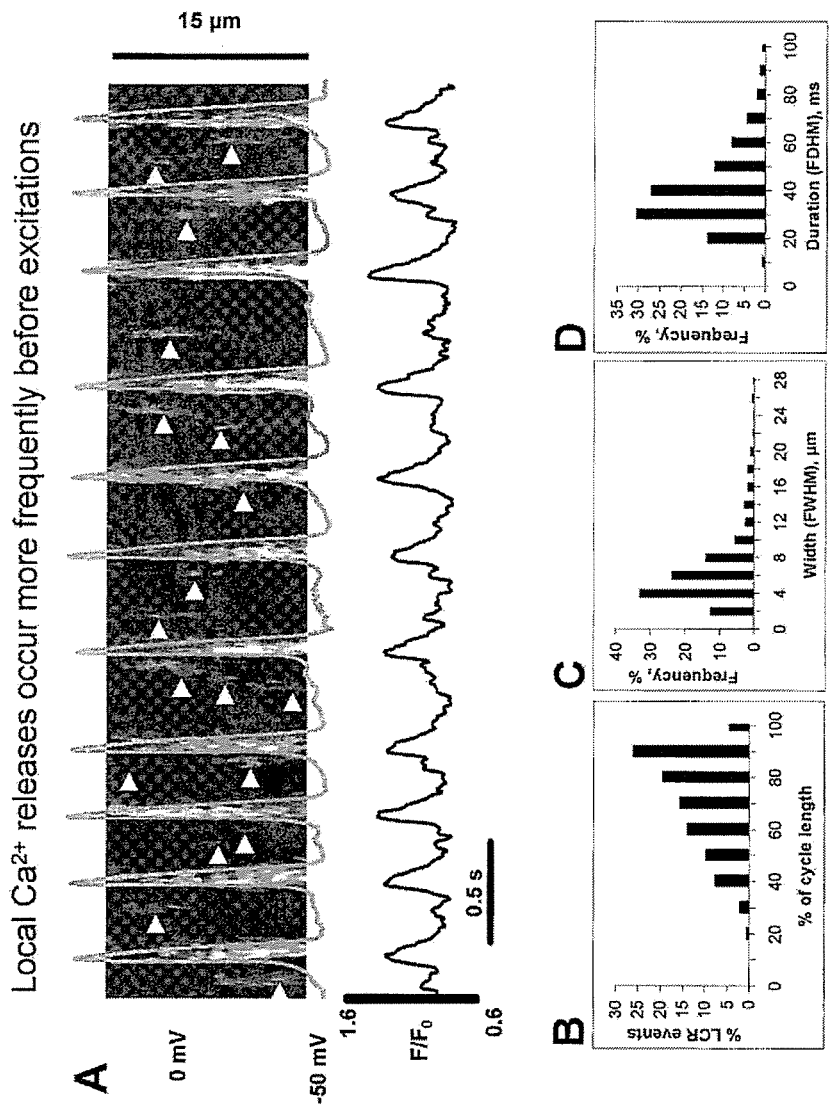
FIG. 3 shows Local $Ca^{2+}$ releases (LCRs) emerge during diastole peaking just before each membrane excitation. Panel A shows simultaneous recording of action potentials and scanline images of $Ca^{2+}$ signals in an intact spontaneously beating ESC. LCRs are shown with arrowheads. Also shown is the time course of the normalized fluorescence ($F/F_0$) along the scanline. Panels B and C show histograms of LCRs size (FWHM) and duration (FDHM). Panel D shows probability of LCR occurrence as a function of the relative cycle length (CL). Histograms: 423 LCRs of 21 cells.

In spontaneously beating ESCs, spontaneous LCRs are observed by confocal microscope (triangles in FIG. 3, Panel A) during diastolic period, i.e., between APs or between global transients induced by the APs. The LCRs range between 2 and 28 μm (5.94+/−0.24 μm, n=354) in size and 10 to 100 ms (35.98+/−0.84 ms, n=354) in duration (FIG. 3, Panel B and C). The LCRs occur primarily in the second half of the cycle, with the occurrence rate increasing (i.e. becoming gradually more synchronous) before next excitation (peaking at 90% of the cycle FIG. 3, Panel D for 423 LCRs measured in 21 cells).

Example 7

Figure 4:
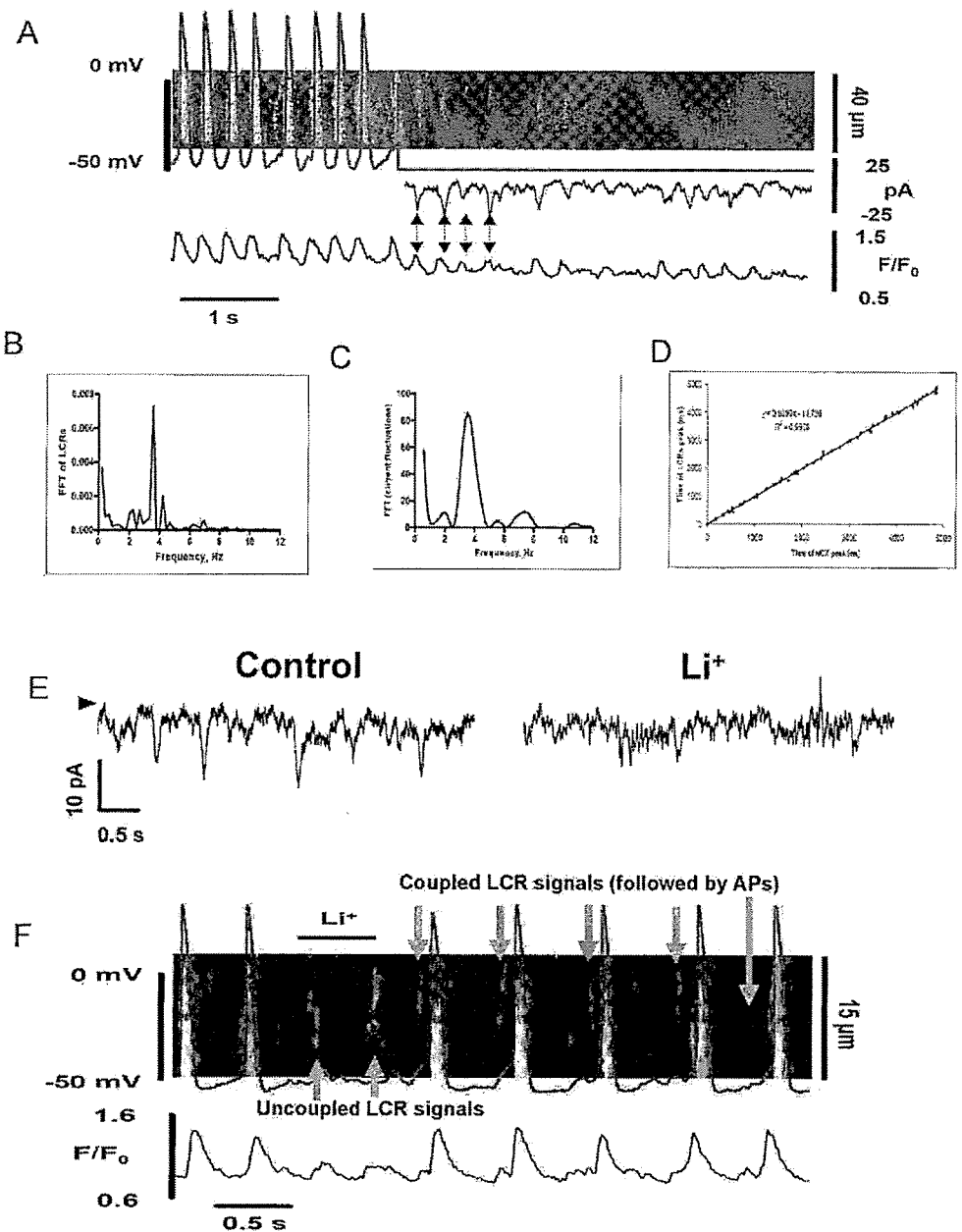
FIG. 4 shows that rhythmic, membrane independent LCRs in intact ESCs produce spikes of inward $Na^+/Ca^{2+}$ exchanger (NCX) current that ignite rhythmic APs. Panel A shows simultaneous recordings of membrane potential or current and confocal scanline image of $Ca^{2+}$ release in a representative spontaneously beating ESC before and during voltage clamp to −50 mV. Panels B and C show Fast Fourier transform (FFT) of LCRs or current during voltage clamp. Panel D shows correlation plot between timing of LCRs and current spikes. E: Inward currents in a cardiomyocyte clamped at −50 mV in control and after exposure to $Na^+$-free $Li^+$-containing solution inhibiting NCX function. Panel F shows simultaneous recording of $Ca^{2+}$ signals and APs in a spontaneously-active ESC during rapid and brief superfusion with a $Na^+$-free solution ("$Li^+$").

Ticks of $Ca^{2+}$ Clock Generate Spikes of Inward NCX Current that Ignite Rhythmic Excitations When activation of ion channels and APs are disabled by voltage clamp at −50 mV, spontaneous LCRS for at least 5 s were observed (FIG. 4, Panel A). Similar to the skinned cell configuration (FIG. 2), the wavelet-like LCRs under voltage clamp were rhythmic with a dominant frequency ranging from 2 to 6 Hz (FIG. 4, Panel B). Under voltage clamp, LCRs generated spikes of inward current (FIG. 4, Panel A, middle). Those spikes were rhythmic with the same dominant frequency as the LCRs (compare FFTs in FIG. 4, Panels B and C); and the timings of current spikes were closely correlated ($R^2$=0.9986) with the respective timings of the LCR peaks (see plot in FIG. 4, Panel D and arrows connecting current and $Ca^{2+}$ signal peaks in FIG. 4, Panel A). Since activation of any voltage-gated membrane currents were excluded under voltage clamp, the same rhythmicity and the close correlation between LCRs and current spikes indicate a close cause-effect relationship between the two. It was determined under the voltage clamp whether LCRs can cause the current spikes via NCX activation. The high-amplitude current spikes (ranging 10 to 20 pA in control) disappeared when $Na^+$ was substituted by $Li^+$ inhibiting NCX function, and the residual small spikes (if any) became comparable with the current noise of about 5 pA) under these conditions (FIG. 4E). To test the importance of these currents for spontaneous beating, $Na^+$-free, lithium solution ($Li^+$ spritz) was briefly applied (for ~1 s) to the patch-clamped spontaneously beating cells under zero-current clamp and simultaneously imaged intracellular $Ca^{2+}$ by confocal microscope (FIG. 4, Panel F). This temporary NCX inhibition resulted in excitation failure (no APs) whereas rhythmic LCRs continued (similarly to voltage clamp experiment; see FIG. 4, Panel A), indicating that the LCR-initiated, NCX-mediated current spikes couple LCRs and the rhythmic excitations.

For the first time here, it is directly shown that rhythmic LCRs (FFT in FIG. 4, Panel B) activate spikes of inward NCX current to ignite rhythmic APs in ESCs: in voltage clamped cells, those current spikes were strongly correlated with LCRs and blocked by $Na^+$-free medium (FIG. 4, Panels A to E); in current clamped cells, short NCX blockage prevented spontaneous AP generation (FIG. 4, Panel F).

These results show that $Ca^{2+}$ clock that interacts with the sarcolemma in ESCs via activation of NCX rather than a nonselective cation current. This LCR→NXC coupling mechanism is similar to that found in sinoatrial node cells and early embryonic cardiomyocytes: $Na^+$ free solution reportedly reduced membrane potential oscillations in current clamp, indirectly indicating a role of NCX in automaticity of these immature heart cells. These results showed the critical importance of integration of the membrane and intracellular mechanisms of automaticity, and identified the specific biophysical ($I_{CaL}$→LCRs→NCX→$I_{CaL}$) and biochemical (via cAMP and PKA) mechanisms of their strongly coupled function.

Example 8

Membrane Clock Enhances $Ca^{2+}$ Clock: LCRs are Synchronized by Prior $I_{CaL}$ Activation While the concept of SR $Ca^{2+}$ clock/oscillator implies that SR operates as one functional organelle generating rhythmic and strong $Ca^{2+}$ signals, in reality SR is spread within cell interior and LCRs are generated by local $Ca^{2+}$ oscillators of the multiple SR fragments in different parts of the cells. Thus, the concept of subcellular $Ca^{2+}$ clock as one functional entity implies that these local $Ca^{2+}$ oscillators operate synchronously. It was then tested if $I_{CaL}$ could synchronize multiple LCRs (i.e., local $Ca^{2+}$ oscillators) via calcium-induced calcium release (CICR) to insure functional integrity of the entire SR and strong NCX currents for the AP ignition described above. LCRs were measured simultaneously in different cell locations after depolarization pulses were applied in voltage-clamped cells to activate $I_{CaL}$ for 200 ms. The result showed that the LCRs, despite their slightly different intrinsic frequency in each location (e.g., slow, intermediate, and fast local oscillators in the same cell in FIG. 5), always evolved highly synchronously during their first several cycles after $I_{CaL}$ activation and its CICR (FIG. 5) until they eventually go out of phase. This pattern of LCR synchronization was highly reproducible (tested in 8 cells), with the number (2 to 8) of synchronized LCR firings depending upon the difference of the intrinsic rate of the local $Ca^{2+}$ oscillators. Suppression of spontaneous beating produced in the presence of partial pharmacological blockade of $I_{CaL}$ by 200 nM of nifedipine was preceded by a temporal phase (of about 1 min duration) with substantial CL variability (tested in 6 cells, not shown).

Figure 5:
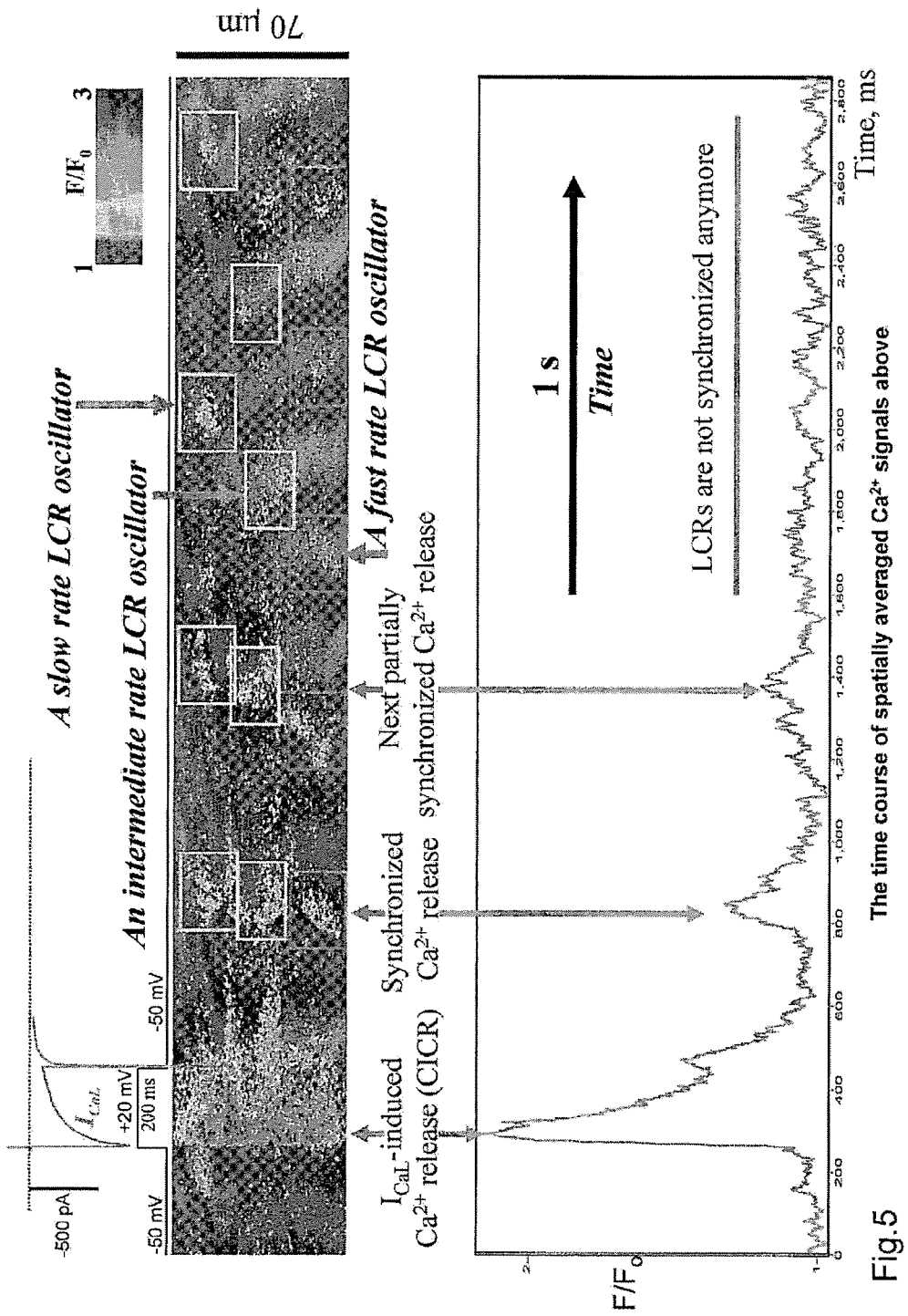
FIG. 5 shows that $I_{CaL}$ triggers $Ca^{2+}$-induced $Ca^{2+}$ release (CICR) and thereby synchronizes phases of local $Ca^{2+}$ oscillators (generating LCRs) under voltage clamp resulting in strong average $Ca^{2+}$ release throughout the cell. Subsequent average releases decrease, as $Ca^{2+}$ oscillators go out of phase.

These results established this $Ca^{2+}$ release synchronization mechanism, underlying functional integrity of the SR (FIG. 5). These results also showed that LCRs cannot synchronize themselves without the sarcolemma "help" of $I_{CaL}$: LCRs can easily go out of phase under voltage claim at −50 mV when $I_{CaL}$ activation is disabled (FIG. 5). These interactive (membrane←→SR) $Ca^{2+}$ oscillations in ESCs are different from those described previously under KCl depolarization: The current results showed a novel physiological function of L-type $Ca^{2+}$ channels (in addition to EC coupling in myocytes), i.e., $I_{CaL}$ synchronizes LCRs in pacemaker cells.

These results demonstrated that the two-way, cycling interactions of $Ca^{2+}$ and membrane clocks ($I_{CaL}$→LCRs→NCX→$I_{CaL}$) are critically important for the ability of ESCs to generate rhythmic APs. Pharmacological inhibition of LCRs or uncoupling of LCRs from membrane function results in arrhythmic beating, culminating in cessation of automaticity or extremely rare (i.e., non-physiological) and irregular beating (FIG. 6; FIG. 4, Panel F).

Example 9

Figure 6:
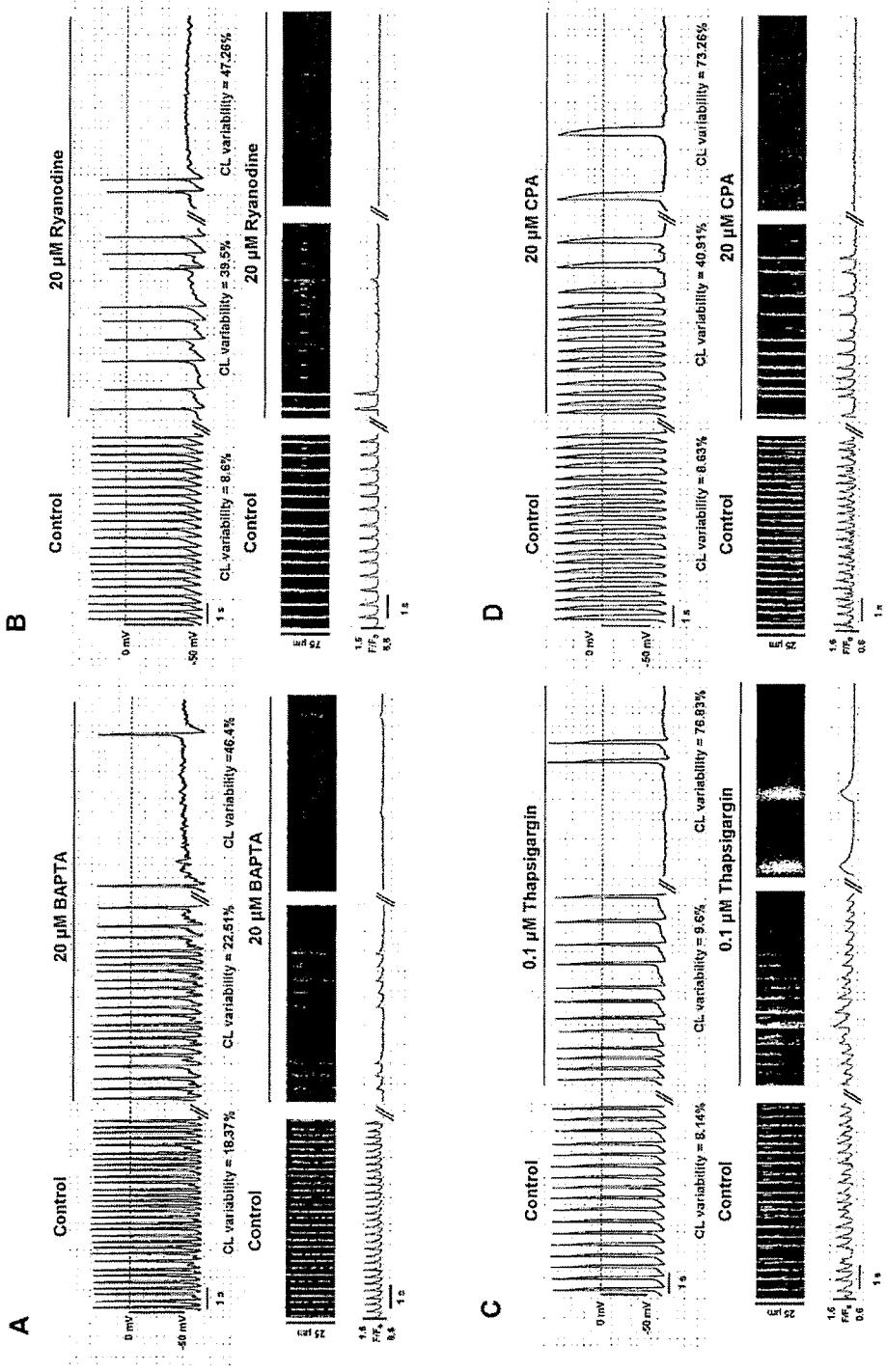
FIG. 6 shows that $Ca^{2+}$ clock is crucial for rhythmic AP firing: Strong $Ca^{2+}$ buffering (Panel A) or interfering with $Ca^{2+}$ release (Panel B) or $Ca^{2+}$ pumping (Panel C and Panel D) result in irregular beating often culminating in cessation of automaticity. Shown are recordings of spontaneous APs and confocal line scan images of representative ESCs prior to and during exposure of the drugs (including an intermediate stage with irregular beating). Cycle length (CL) variability index (defined as 100%×CL standard deviation/CL mean) is shown for APs in control, in transition, and after reaching a steady-state after drug application.

$Ca^{2+}$ Clock is Driven by High Basal cAMP/PKA Activity and is Required for Rhythmic AP Firing Generation of rhythmic APs by membrane clock requires functional SR generating LCRs. To show this, the normal SR function was interfered with by buffering intracellular $Ca^{2+}$ with BAPTA-AM, disabling RyR function with ryanodine, or inhibiting SERCA with thapsigargin or cyclopiazonic acid (CPA) (FIG. 6). All of the above interventions inhibited LCRs. As LCRs decreased, spontaneous AP firing and $Ca^{2+}$ transients became irregular, culminating in cessation of automaticity or in extremely rare and irregular beating.

Figure 7:
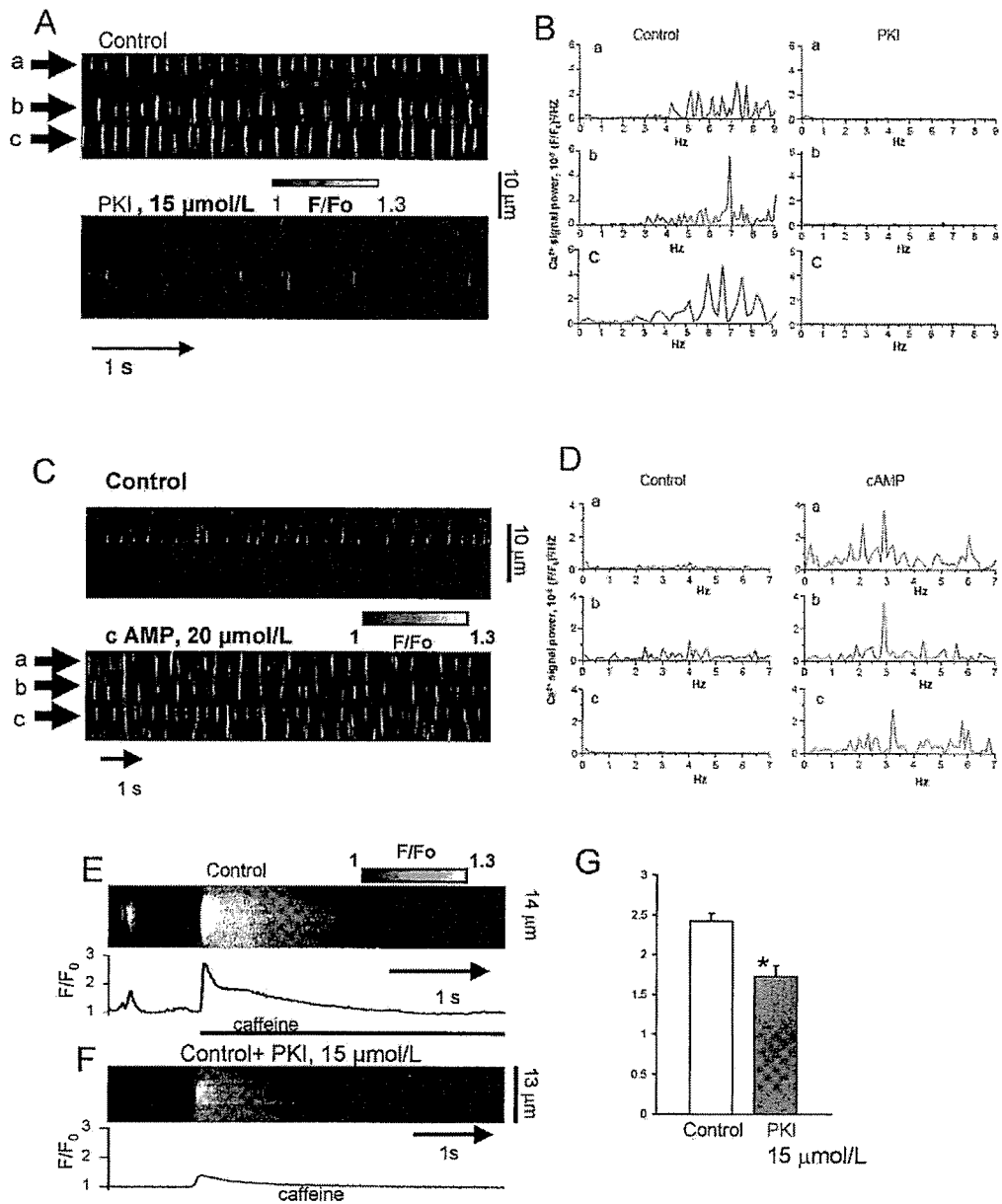
FIG. 7 shows that cAMP/PKA signaling is required for LCRs and $Ca^{2+}$ clock function. Panels A-D: Confocal line-scan images, and FFTs (of 18 s recording) in three cell locations (arrows) of a representative saponin-skinned ESC before (top) and after (bottom) superfusion with 15 µmol/L PKI, a selective PKA inhibitor, or stimulation with 20 µmol/L cAMP. Panels E and F: Confocal line-scan images and $Ca^{2+}$ transients induced by rapid application of 20 mmol/L of caffeine to skinned ESC in control condition and after incubation with 15 µmo/L PKI. Panel G: The average amplitude of caffeine-induced $Ca^{2+}$ transients in control conditions (n=7 cells) and 15 µmol/L PKI (n=7 cells), $P<0.001$.

The following results showed basal cAMP-dependent PICA activation contributed to generation of spontaneous LCRs in ESCs. In saponin-skinned ESCs, a specific PKA inhibitor PKI substantially decreased the number of LCRs (FIG. 7, Panels A and B), with the remaining LCRs becoming less frequent, smaller in amplitude, and less rhythmic (e.g., $Ca^{2+}$ oscillator in location "b" in FIG. 7, Panel A). In contrast, application of cAMP to skinned cells resulted in the emergence of new local $Ca^{2+}$ oscillators in many cell locations (which were silent before the cAMP boosting); those oscillators, which were present in the control (before cAMP application), became generating LCRs of larger in size and amplitude (e.g., $Ca^{2+}$ oscillator in location "b" in FIG. 7, Panel C). The mechanism of the enhanced $Ca^{2+}$ cycling by the SR in the basal state is likely linked to basal SR Ca$^{2+}$ loading driven by the enhanced intrinsic cAMP/PKA-signaling, because the amplitudes of caffeine-induced transients are significantly (by ~29%) decreased when cells were pretreated with PKI inhibiting PKA signaling (FIG. 7, Panels E to G).

Figure 8:
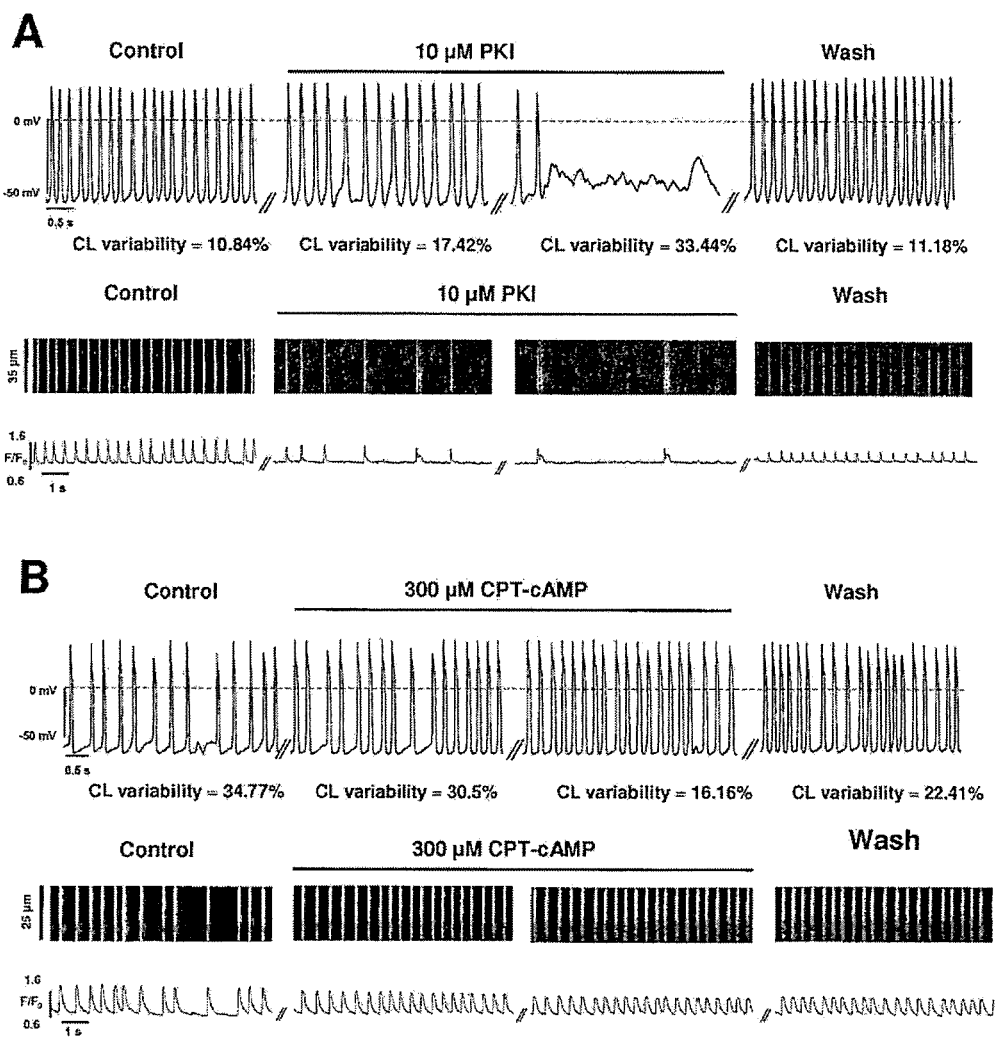
FIG. 8 shows that basal cAMP/PKA activity is crucial for rhythmic spontaneous APs and $Ca^{2+}$ transients of ESCs. Typical example of APs and $Ca^{2+}$ releases recorded in spontaneously beating ESCs before and during superfusion with 10 µmol/L PKI (A) or with 300 µmol/L CPT-cAMP. CL variability index is also shown under respective AP traces.
Figure 9:
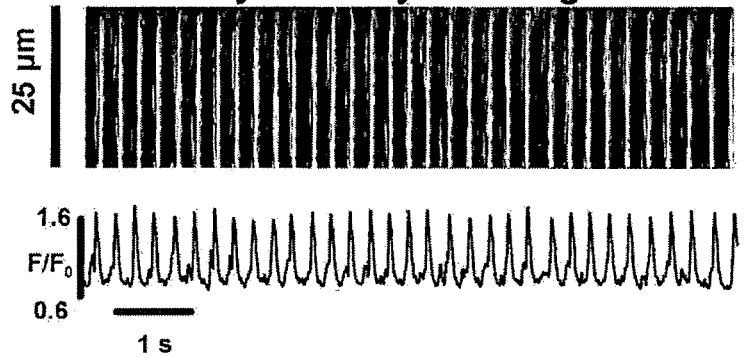
FIG. 9 shows substantial range of CL variability in ESCs. Panels A and B: Examples of rhythmically and irregularly beating cells. Panel C: Distribution of CL variability measured in 21 ESCs.
Figure 9:
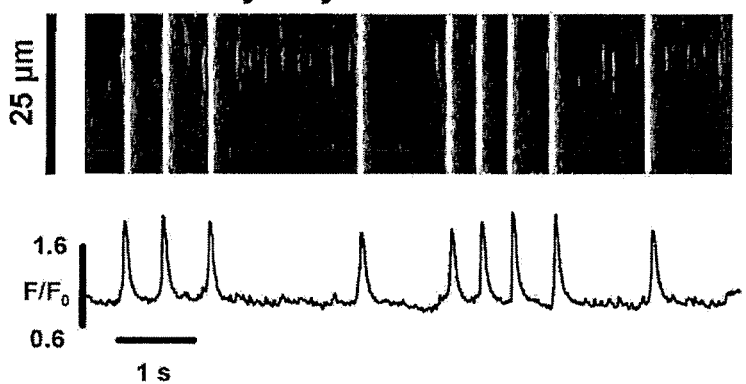
Figure 9:
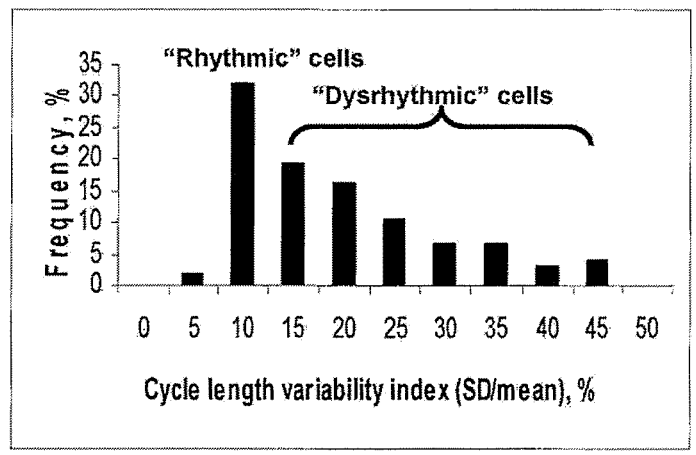

In spontaneously beating ESCs PKA inhibition with either H89 (10 μmol/L) or PKI resulted in irregUlar APs or cessation of automaticity (FIG. 8, Panel A). In contrast, enhancing cAMP/PKA signaling by application of a membrane-permeable cAMP (CPT-cAMP) converted irregularly beating ESCs to rhythmic pacemakers (FIG. 8, Panel B). More specifically, in cells with irregular beating the cycle length (CL) variability index (defined as 100%×CL standard deviation/CL mean) significantly decreased from 23.98+/−4.82% to 11.23+/−2.68% (P<0.05). For comparison, results showed that ESCs exhibit a broad range of CL variability index varying from about 5-10% (rhythmic cells) to 45% (irregularly beating cells (FIG. 9).

High expression of major Ca$^{2+}$ cycling proteins, such as L-type Ca$^{2+}$ channels, NCX, SERCA2, IP3 receptors, and RyRs resulting in both Ca$^{2+}$ transients and wavelet-like, diastolic LCRs have been observed by others in mouse and human ESCs. The results shown here indicates that sarcolemmal pacemaker mechanisms in human ESCs, such as $I_f$, $I_{CaL}$, or window $I_{Na}$ ("membrane clock" in FIG. 1), will likely require integration with their Ca$^{2+}$ clock ("local Ca$^{2+}$ events" in human cells (13) to insure rhythmic and responsive pacemaker function.

$I_{CaL}$ regulation in ESCs likely have high intrinsic PlCA activity and high intrinsic adenylylcyclase activity, which is counterbalanced by high intrinsic activity of phosphodiesterase and phosphatases. The high basal level of cAMP/PKA activity is critical for automaticity of ESCs (FIG. 1), as it enhances not only basal $I_{CaL}$ and If but also basal Ca$^{2+}$ cycling resulting in abundant spontaneous LCRs comprising Ca$^{2+}$ clock (FIGS. 7 and 8). The novel finding here is that it is basal intrinsic PKA activation that maintains Ca$^{2+}$ SR loading (FIG. 7, Panel E to G), and thereby causes the spontaneous Ca$^{2+}$ release.

The results herein indicate that the expression of multiple sarcolemmal and SR proteins (ion channels, pumps, exchangers, and regulatory proteins; see FIG. 1) must be balanced in ESC biological pacemakers to insure the enhanced functionality of Ca$^{2+}$ and membrane clocks and their strong coupling, resulting in rhythmic beating. More specifically, these results suggest that the reasons for irregular beating of ESCs include not only increasing expression of IK1, stabilizing the resting potential, but also a decreased expression and/or activity of Ca$^{2+}$ cycling proteins (including due to decrease in intracellular cAMP level during development and/or increased phospholamban expression). Thus, targeting IK1 in biological pacemakers need be complemented with targeting Ca$^{2+}$ clock proteins and/or regulatory proteins to maintain the high level of basal cAMP/PKA activity enhancing both clocks and their interaction (FIGS. 1, 7, and 8). The results herein (FIG. 8) showed that irregularly beating ESCs are easily converted to rhythmic pacemaker-like cells by membrane permeable cAMP; and, vice-versa, rhythmical beating stops when basal PKA activity is inhibited.

The high basal level of cAMP/PKA activity is also likely important for responsive function of the biological pacemakers: The ESC pacemaker rate regulation (both increase and decrease) can be mediated via L-type Ca$^{2+}$ channels, If, and Ca$^{2+}$ cycling proteins generating basal LCRs (FIGS. 1, 7, and 8), i.e., similar to results that were previously found by others in atrial node cells.

Example 10

Vector

Based on the above described mechanism, applicants created a vector that produces a biological pacemaker via permanent and inducible activation of Ca$^{2+}$-activated Adenylate cyclase 8 (AC8) within targeted cells. AC8 produces cAMP that initiates the chain of interactions within targeted cells resulting in a positive feedback loop to activate more AC8 via its intrinsic Ca$^{2+}$-activated property that can be summarized as follows:

Ca_activ.AC8→cAMP→PKA→PLB&RyR&$I_{CaL}$→moreCa→more Ca_activ.AC8

Thus sustained activation of AC8 via this mechanism strongly couples Ca$^{2+}$ and membrane clocks and thereby creates a robust, sustained biological pacemaker (similar to that described in FIG. 8B with membrane permeable cAMP, but only cAMP in this case is permanently produced within the targeted cells).

The inducible activation property (with Doxicicline) was implemented in the construct only in order to simplify laboratory testing (i.e. for convenient comparison of cell activity before and after induction of AC8 expression/activation). The parts for red and green fluorescent proteins were also included into the construct in order to monitor the construct function: to trace transfected cells and to detect AC8, respectively. In case of future application of this virus type technology to patients, these additional features can be easily excluded from the construct.

The vector pLenti6-R4R2-V5-DEST from Invitrogen was used to create a target vector. To original backbone was introduced following elements:

cPPT—central polypurine tract/central termination sequence which improve transferring viral RNA to nuclear hereby increase viral titer;

PGK—phosphoglycerate kinase promoter: PCR was performed with a mixture of 4 primers: CTACCGGG-TAGGGGAGGCGC (SEQ ID NO: 1); GTC-GAAAGGCCCGGAGATGA (SEQ ID NO: 2); GCTGTGCCCCAGTTTGCTAG (SEQ ID NO: 3) and TCATCTCCGGGCCTTTCGACACCGGTCGCCAC-CATGG (SEQ ID NO: 4). The templates were pTurboFP635N (Eurogen) and pLVX-Tight-Puro-Luc (Clonetech). The PCR product was integrated to pENTR5'-topo by a TOPO reaction (Invitrogen);

TurboFP635—Red fluorescent protein from Eurogen. PCR was performed with a mixture of 4 primers: CTACCGGGTAGGGGAGGCGC (SEQ ID NO: 1); GCTGTGCCCCAGTTTGCTAG (SEQ ID NO: 3); TACTTAGTTACCCGGGGAGC (SEQ ID NO: 5) and CTAGCAAACTGGGGCACAGCGAGGGCAGAG-GAAGTCTTCTAACATGC GGTGACGTGGAGGA-GAATCCCGGCCCTATGTCTAGACTGGA-CAAGAG (SEQ ID NO: 6). The templates were pENTR-PGK-Turbo-L4R1 and pTET-On-advance (Clonetech). The PCR product was integrated to pENTR5'-topo by the TOPO reaction (Invitrogen).

T2A—self digested peptide which allow to produce two separated proteins from same mRNA;

rtTA-adv—from Tet-ON advance system (Clonetech) allow to activate mRNA synthesis in the presence Doxicicline;

TRE promoter—promoter which could be activated by rtTA or tTA proteins in the presence/absence Doxycicline. PCR was performed with the following primers: GGGGACAAGTTTGTACAAAAAAGCAGGCT-TAATTTTTTTCACTGCCTC G (SEQ ID NO: 7) and GGGGACAACTTTTGTATACAAAGTTGTAG-
GCTGGATCGGTCCCGG (SEQ ID NO: 8). The template was the vector pTRE2pur-HA (Clonetech). The PCR product was recombined with pDONR221-P1P5r (Invitrogen) using the BP reaction.

TagGFP2—Green fluorescent protein from Eurogen PCR was performed with the following primers: GGGGA-CAACTTTGTATACAAAAGTTGTGCGCCACCAT-GAGCGGGGG (SEQ ID NO: 9) and GGGGA-CAACTTTGTATAGAAAAGTTGGGTGCCCCTGT-ACAGCTCGTCC AT (SEQ ID NO: 10). The template was pTaqGFP2C (Eurogen). The PCR product was recombined with pDONR221-P5P4 (Invitrogen) using a BP reaction.

ADCY8—CDS of Adenylate cyclase 8 from Open Biosystems. PCR was performed with the following primers: GGGGACAACTTTTCTATACAAAGTTGCTT-GAGGGCAGAGGAAGTCTTC
TAACATGCGGTGACGTGGAGGAGAATCCCG-GCCCCGCCACCATGGAG CTCTCCG (SEQ ID NO: 11) and GGGGACAACTTTATTATACAAAGTT-GTCCCTATGGCAAATCAGATTTG TC (SEQ ID NO: 12). The template was pLoc-ADCY8 (Open Biosystems). The PCR product was recombined with pDONR221-P4rP3r (Invitrogen) using tahe BP reaction.

Figure 10:
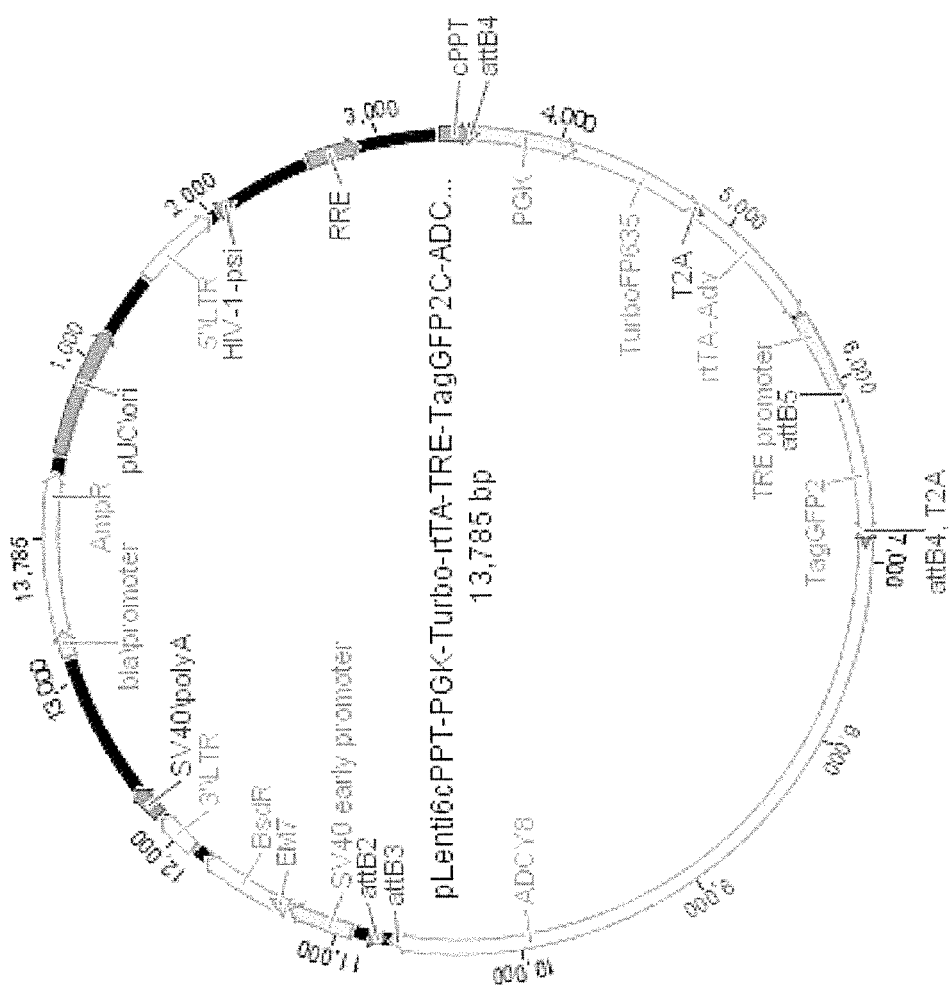
FIG. 10 shows a vector map of used for packaging virus.

MCS: PCR was performed with the following primers: GGGGACAACTTTGTATAATAAAGTTGCT-GCTAGCGCTACCGGACTC (SEQ ID NO: 13) and GGGGACCACTTTGTACAAGAAAGCTGGG-TAACCGGTGGATCCCGGGC (SEQ ID NO: 14). The template was pTurboFP635N (Eurogen). The PCR product was recombined with pDONR221-P3P2 (Invitrogen) using a BP reaction The resulting vector is shown in FIG. 10. The insert of the final vector was confirmed by cDNA sequencing.

The final packaging of viral particles was carried out using the Lenti-X HTX system (Clonetech). The harvested virus was concentrated using the Lenti-X Concentrator (Clonetech) and reconstituted in P19 cultivation Media.

Example 11

P19 Transfecting and Differentiation

Embryonic Carcinoma Cells P19 cells P19 embryonic carcinoma cells (American Type Culture Collection) were plated in 6 well plate with concentration 100,000 cells per well. On the next day, the cells were transfected directly with the concentrated virus. After incubation for one day, the cells were differentiated into cardiomyocytes by the standard "hanging drops" technique. For this purpose, hanging drops were made with 400 cells/drop in P19 Differentiation Media supplemented with 1% DMSO. After 2 days of incubation at 37° C. at 5% $CO_2$, the hanging drop were washed in Differentiation Media without DMSO and were incubated in a floating state for 5 days. On Day 7, the resulting embryoid bodies (EBs) were plated in Differentiation Media in multichambered microscope slides.

Two days later, measurements of the beating rates of the beating areas of the EBs were performed. Measurements of the same beating areas were performed prior to and 4 hours after treatment of EBs with Doxycycline (final concentration: 1 microgram/ml) to activate ADCY8 in the transfected gene construct. The beating activity of each EB was recorded with a linescan of transparency at 37° C. using a live imaging microscope (work carried out in conjunction with Katherine Baty, Center for Biologic Imaging, University of Pittsburgh). Line scans were further analyzed by APAnaliser program (Victor Maltsev, NIA/NIH) to measure duration of each contraction cycle (Cycle Length, CL).

Figure 11:
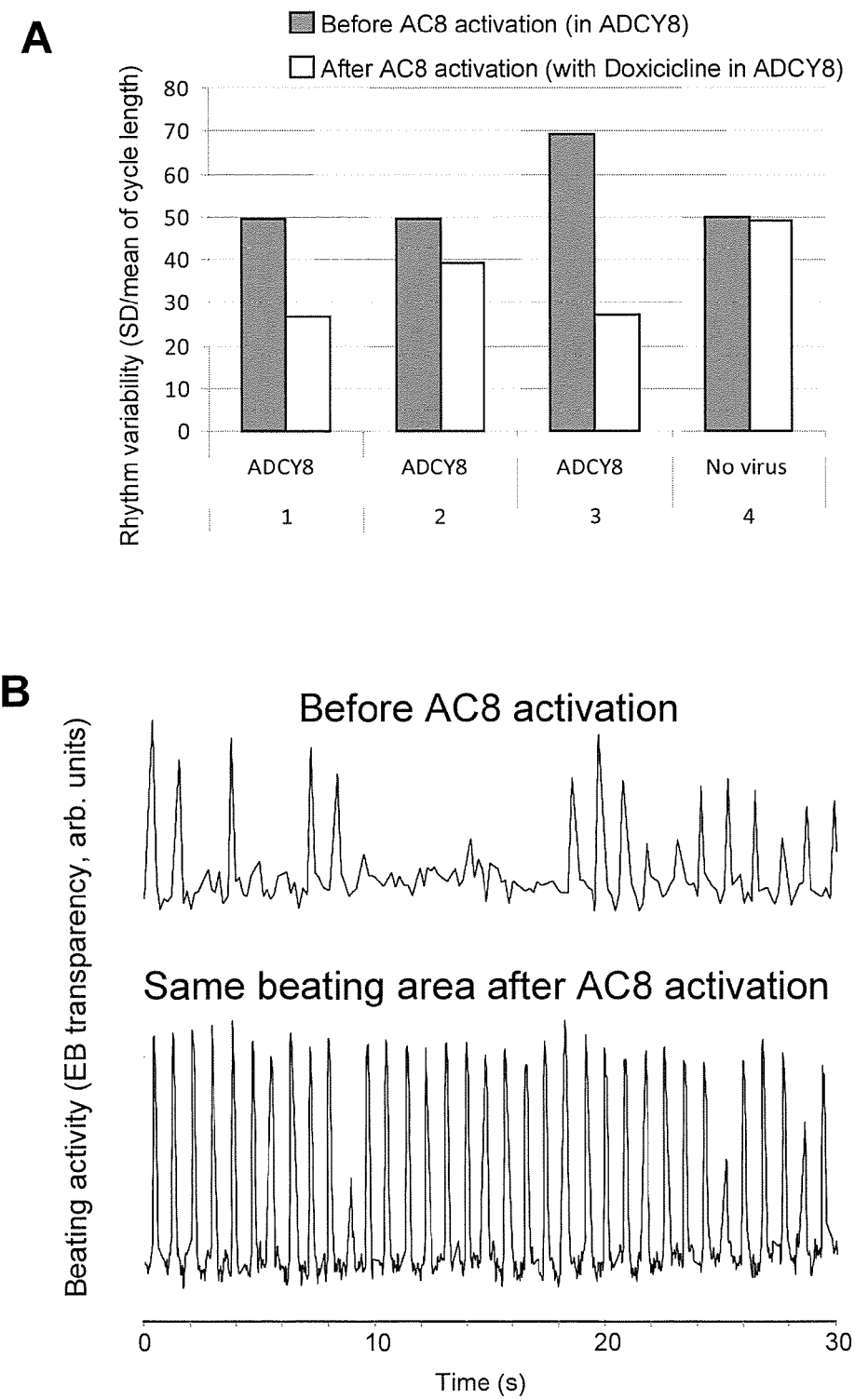
FIG. 11 shows how the variability index (SD/mean of cycle length) decreased in three EBs (ADCY8 1-3), but almost no change was observed after this time in control EBs with no virus ("No virus").

The beating activity of each EB was recorded with line scan of transparency at a physiological temperature (37° C.) using a live imaging microscope. Line scans were further analyzed by a program to measure duration of each contraction cycle length (CL). Measurements of the same beating areas were performed before and 4 hours after EBs treatment with Doxicicline (final concentration 1 mkg/ml) to activate AC8. Simultaneously, control EBs were measured without virus treatment (with the same 4 hours time interval). Results are shown in FIG. 11.

Four hours after treatment of EB's with Doxycycline to activate ADCY8 in virus-infected cells, the rhythm of spontaneous beating EB areas was substantially and significantly improve. For each beating area, the variability index (VI: SD/mean) was calculated. The VI is a measure of the consistency (rhythmicity) of the beating rate, with a lower VI being better (i.e. more consistent) than a higher VI.

Example 12

CaMK II Expression

This example discusses creation of biological pacemakers using expression of CaMK II. Specifically, it describes a new method of increasing CaMK II expression in targeted cells and an experiment using this method to show efficacy by increasing CaMK II expression to create biological pacemaker activity or enhance/supplement biological pacemaker activity induced by other means.

The CaMK II δC is the CaMK II isoform that phosphorylates proteins of both $Ca^{2+}$ and membrane clocks and regulates the heart rate. Thus, the method includes expression of this specific isoform in the targeted cells using the same virus technology as described in Example 10 that was used to create ADCY8 carrying vector. The difference is only in one of 5 entry vectors. This vector is created by standard BP reaction protocol (Invitrogen). PCR amplification is performed with primers and with CaMK2Dc carrying clone from Open Biosystems (Cat #OHS5830-101189215 or OHS5830-100998687) as a template. All following steps are the same as used for ADCY8 creation in Example 10. Insert of final vector is then sequenced.

The P19 cells are transfected and differentiated into cardiac-like cells as described in Example 11, but using the virus particles carrying CaMK II δC isoform described above. After induction of CaMK II δC expression the rhythm of spontaneous EB beating is expected to improve similar to that found with AC8 expression shown in FIG. 11.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of producing a biological pacemaker, comprising administering in vivo a viral vector comprising a nucleic acid that encodes an adenylyl cyclase into electrically excitable cardiomyocytes of the heart of a patient, wherein the administering comprises contacting the viral vector with one or more cardiomyocytes of the patient, wherein the administration of the nucleic acid provides for expression of the corresponding adenylyl cyclase protein in an amount sufficient to induce rhythmic local $Ca^{2+}$ releases in said cells which results in a sustained rhythmic and regular beating of the cardiomyocyte expressing the adenylyl cyclase protein.

2. The method of claim 1, wherein said cardiomyocytes are located in the right ventricle, the right atrium, the sinoatrial node or the atrioventricular node.

3. The method of claim 1, wherein said cardiomyocytes exhibit spontaneous rhythmic excitation after the expression of the adenylyl cyclase protein.

4. The method of claim 1, wherein said adenylyl cyclase protein is selected from the group of adenylyl cyclases consisting of a $Ca^{2+}$-activated adenylyl cyclase type 1, $Ca^{2+}$-activated adenylyl cyclase type 8, and a combination thereof.

5. The method of claim 1, wherein said cardiomyocytes exhibit spontaneous, rhythmic, and sustained excitations after the expression of the adenylyl cyclase protein.

6. The method of claim 1, wherein said adenylyl cyclase protein modulates at least one whole cell $Ca^{2+}$ clock and at least one membrane clock in said cardiomyocytes.

7. The method of claim 1, wherein the viral vector is selected from the group consisting of an adenoviral associated vector, a herpes vector, and a retroviral vector.

8. The method of claim 1, wherein the viral vector further comprises at least one control sequence selected from the group consisting of a transcription initiation region, a transcription termination region, an adenoviral associated vector inverted terminal repeat sequence, a promoter, and an enhancer.

9. The method of claim 8, wherein the promoter or enhancer element or both are cardiac-specific.

* * * * *

UNITED STATES PATENT AND TRADEMARK OFFICE
CERTIFICATE OF CORRECTION

PATENT NO.      : 9,506,032 B2
APPLICATION NO. : 13/322066
DATED           : November 29, 2016
INVENTOR(S)     : Victor Maltsev et al.

Page 1 of 1

It is certified that error appears in the above-identified patent and that said Letters Patent is hereby corrected as shown below:

On the Title Page

(75) Inventors should read: "Victor Maltsev, Parkville, MD (US);
Edward G. Lakatta, Bel Air, MD (US);
Ihor Zahanich, Rosedale, MD (US);
Syevda Sirenko, Baltimore, MD (US);
Maxim Mikheev, Clairton, PA (US);
Yoram Vodovotz, Sewickley, PA (US)"

(73) Assignees should read: "The United States of America, as
represented by the Secretary,
Department of Health and Human
Services, Bethesda, MD (US);
University of Pittsburgh---of The
Commonwealth System of Higher
Education, Pittsburgh, PA (US)"

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*